(12) United States Patent
Pereira da Cunha et al.

(10) Patent No.: US 7,888,842 B2
(45) Date of Patent: Feb. 15, 2011

(54) ULTRA-THIN FILM ELECTRODES AND PROTECTIVE LAYER FOR HIGH TEMPERATURE DEVICE APPLICATIONS

(75) Inventors: Mauricio Pereira da Cunha, Orono, ME (US); Robert J. Lad, Glenburn, ME (US); David Joseph Frankel, Orono, ME (US); George Paul Bernhardt, IV, Hampden, ME (US); Thomas Moonlight, Dover-Foxcroft, ME (US)

(73) Assignee: University of Maine System Board of Trustees, Bangor, ME (US)

( * ) Notice: Subject to any disclaimer, the term of this patent is extended or adjusted under 35 U.S.C. 154(b) by 842 days.

(21) Appl. No.: 11/891,081

(22) Filed: Aug. 9, 2007

(65) Prior Publication Data

US 2010/0181869 A1 Jul. 22, 2010

Related U.S. Application Data

(63) Continuation-in-part of application No. 11/046,712, filed on Jan. 31, 2005, now Pat. No. 7,285,894.

(60) Provisional application No. 60/544,650, filed on Feb. 13, 2004.

(51) Int. Cl.
*H01L 41/08* (2006.01)
(52) U.S. Cl. ........................ 310/324; 363/364
(58) Field of Classification Search .................. 310/363, 310/364, 313 A
See application file for complete search history.

(56) References Cited

U.S. PATENT DOCUMENTS

| | | |
|---|---|---|
| 4,249,418 A | 2/1981 | Ebata |
| 4,399,441 A | 8/1983 | Vaughan et al. |
| 5,446,452 A | 8/1995 | Litton |
| 5,686,779 A | 11/1997 | Vig |
| 5,744,902 A | 4/1998 | Vig |
| 5,821,673 A | 10/1998 | Pisarevsky et al. |
| 5,844,347 A | 12/1998 | Takayama et al. |
| 5,894,251 A | 4/1999 | Taguchi et al. |
| 5,905,325 A | 5/1999 | Naumenko et al. |
| 5,912,602 A | 6/1999 | Takagi et al. |
| 5,917,265 A | 6/1999 | Naumenko et al. |
| 6,005,325 A | 12/1999 | Inoue et al. |
| 6,031,315 A | 2/2000 | Abbott |
| 6,054,794 A | 4/2000 | Naumenko et al. |
| 6,084,333 A | 7/2000 | Inoue et al. |

(Continued)

FOREIGN PATENT DOCUMENTS

JP 09-069748 A 3/1997

(Continued)

OTHER PUBLICATIONS

International Search Report dated Jun. 2, 2009 from Korean Intellectual Property Office.

(Continued)

*Primary Examiner*—Mark Budd
(74) *Attorney, Agent, or Firm*—MacMillan, Sobanski & Todd, LLC

(57) ABSTRACT

An ultra-thin film electrode including at least one electrically conductive layer disposed upon an adhesive layer that is carried by a substrate.

33 Claims, 29 Drawing Sheets

U.S. PATENT DOCUMENTS

| | | | |
|---|---|---|---|
| 6,097,131 | A | 8/2000 | Naumenko et al. |
| 6,186,005 | B1 | 2/2001 | Leidl |
| 6,297,580 | B1 * | 10/2001 | Takayama et al. ............ 310/364 |
| 6,317,014 | B1 | 11/2001 | Kadota |
| 6,323,577 | B1 | 11/2001 | Inoue et al. |
| 6,370,955 | B1 | 4/2002 | Tuller et al. |
| 6,429,570 | B1 | 8/2002 | Inoue et al. |
| 6,538,359 | B1 | 3/2003 | Hiraku et al. |
| 6,571,638 | B2 | 6/2003 | Hines et al. |
| 6,998,687 | B2 | 2/2006 | Inoue et al. |
| 7,285,894 | B1 | 10/2007 | Pereira da Cunha |
| 7,652,412 | B2 * | 1/2010 | Nihei ......................... 310/346 |
| 2003/0231082 | A1 | 12/2003 | Takata et al. |
| 2006/0119229 | A1 * | 6/2006 | Koizumi et al. ............. 310/358 |
| 2009/0237468 | A1 * | 9/2009 | Kanemoto .................... 347/70 |
| 2010/0117493 | A1 * | 5/2010 | Hayashi et al. ............. 310/364 |

FOREIGN PATENT DOCUMENTS

KR  10-2002-008743 A  10/2002

OTHER PUBLICATIONS

2007 IEEE Ultrasonics Symposium, 2107-2110 (M. Pereira de Cunha) Oct. 31, 2007 "Enabling Very High Temperature Acoustic Wave Devices for Sensor & Frequency Control Applications".

I.B. Yakovkin et al., Numerical and Experimental Investigation SAW in Lagasite, 1995 IEEE Ultrasonics Symposium, pp. 389-392.

V. P. Plessky et al., Surface Transverse Waves on Langasite, 1998 IEEE Ultrasonics Symposium, pp. 139-142.

Y. Satoh et al., SAW Duplexer Metallizations for High Power Durability, 1998 IEEE Ultrasonics Symposium.

H. J. Whitehouse et al., High Temperature Ultrasonic Devices for Harsh Environments (Abstract), 2000 IEEE Ultrasonics Symposium.

Pereira da Cuna et al., Experimental and Predicted SAW Temperature Behavior of Langatate, 2000 IEEE Ultrasonics Symposium, pp. 245-248.

Pereira da Cuna et al., Pure Shear Horizontal SAW on Langatate, 2000 IEEE Ultrasonics Symposium, pp. 231-234.

Mitch M.C. Chou et al., Investigation of Crystal Growth and Material Constants of Ordered Langasite Structure Compounds, 2001 IEEE Interantional Frequency Control Symposium, pp. 250-254.

Pereira da Cuna et al., LGX Pure Shear Horizontal SAW for Liquid Sensor Applications, Proceedings of the 2002 IEEE Sensors, Jun. 2002.

Pereira da Cuna et al., Surface and Pseudo Surface Acoustic Waves in Langatate: Predictions and Measurements, 2002 IEEE Trans. Ultrason. Ferroecec. Freq. Contr., Sep. 2002, pp. 1291-1299.

Pereira da Cuna et al., High Coupling, Zero TCD SH Wave on LGX, 2002 IEEE Ultrasonics Symposium, Oct. 2002.

Pereira da Cuna et al., High Temperature Surface Acoustic Wave Devices: Fabrication and Characterisation, Electronics Letters, May 15, 2003, vol. 39, No. 10, pp. 818-819.

Pereira da Cuna et al., High Temperature LGS Devices with Pt/WO$_3$ and Pd Sensing films,'2003 IEEE Ultrasonics Symposium, Oct. 2003, pp. 1750-1753.

J. A. Thiele et al., High Temperature SAW Gas Sensor on Langasite, Proceedings of the IEEE Sensors Conference, Oct. 22-24, 2003, pp. 769-772.

J. A. Thiele et al., Dual Configuration High Temperature Hydrogen Sensor on LGS SAW Devices, Proceedings of the IEEE International Ultrasonics 50$^{th}$ Anniversary Joint Conference, Aug. 24-27, 2004.

Jeremy A. Thiele et al., Platinum and Palladium High Temperature Transducers on Langasite, submitted Dec. 16, 2003, accepted Aug. 10, 2004, published in IEEE Transactions on Ultrasonics, Ferroelectrics and Frequency Control, vol. 52, No. 4, Apr. 2005, pp. 545-549.

J. A. Thiele et al., High Temperature LGS SAW Gas Sensor, submitted for publication on Aug. 13, 2004, accepted for publication Mar. 15, 2005, posted on Sensors and Actuators website on May 5, 2005.

* cited by examiner

Cycling exposure to hydrogen with an oxygen baseline. '*' $H_2$ on, 'Δ' $H_2$ off ($f_O$ 84.999 MHz)

Cycling exposure to hydrogen with a nitrogen baseline. '*' $H_2$ on, 'Δ' $H_2$ off ($f_O$ 167.1455 MHz)

FIG. 14  Platinum and zirconium layered films on Sapphire tested to 1000°C

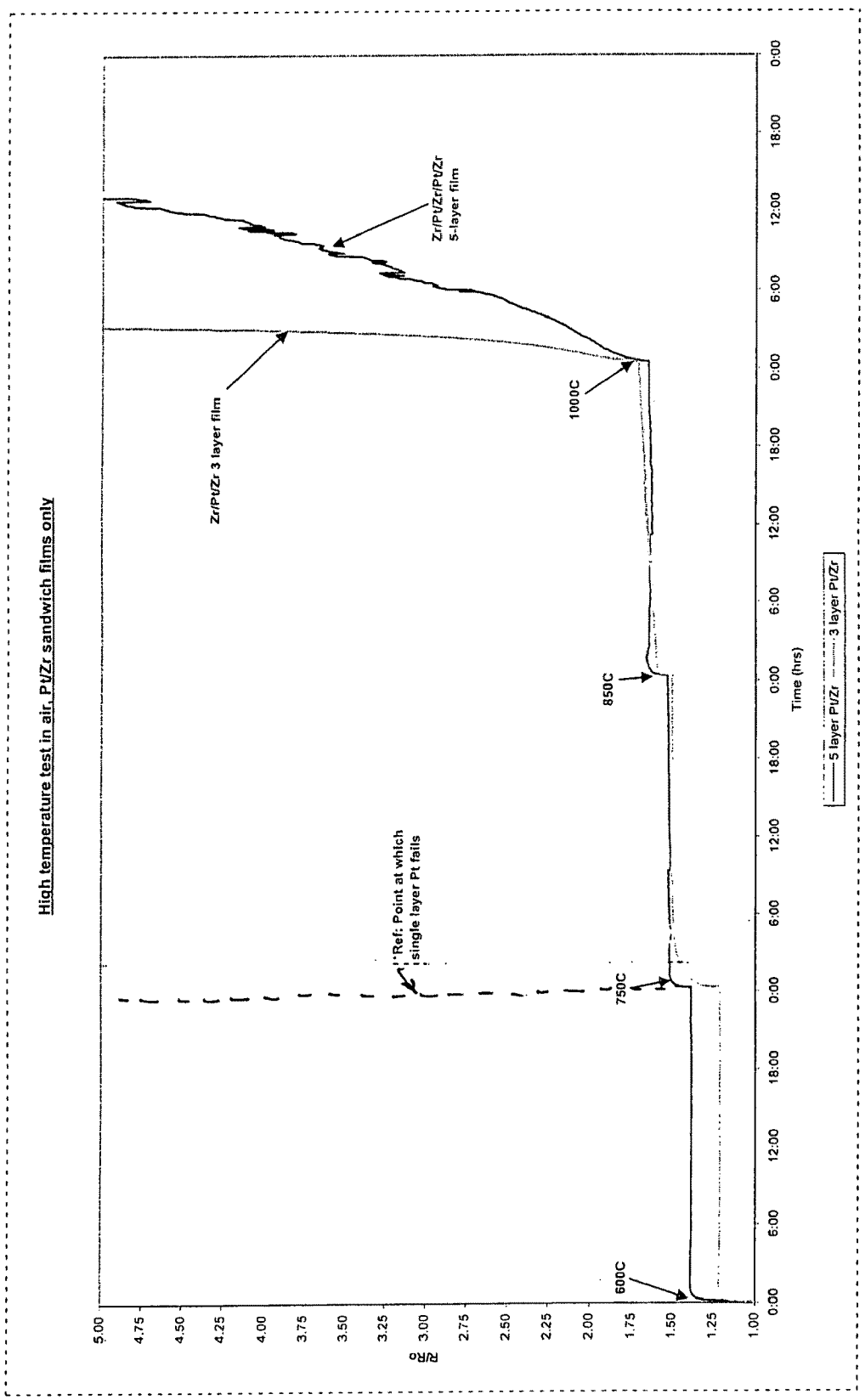
FIG. 16  Platinum and zirconium layered films on Sapphire tested to 1000°C Surface Acoustic Wave Device without a SiAlON protective top layer after being heated to 1000° C for 40 hours Surface Acoustic Wave Device with a SiAlON protective top layer after being heated to 1000° C for 40 hours

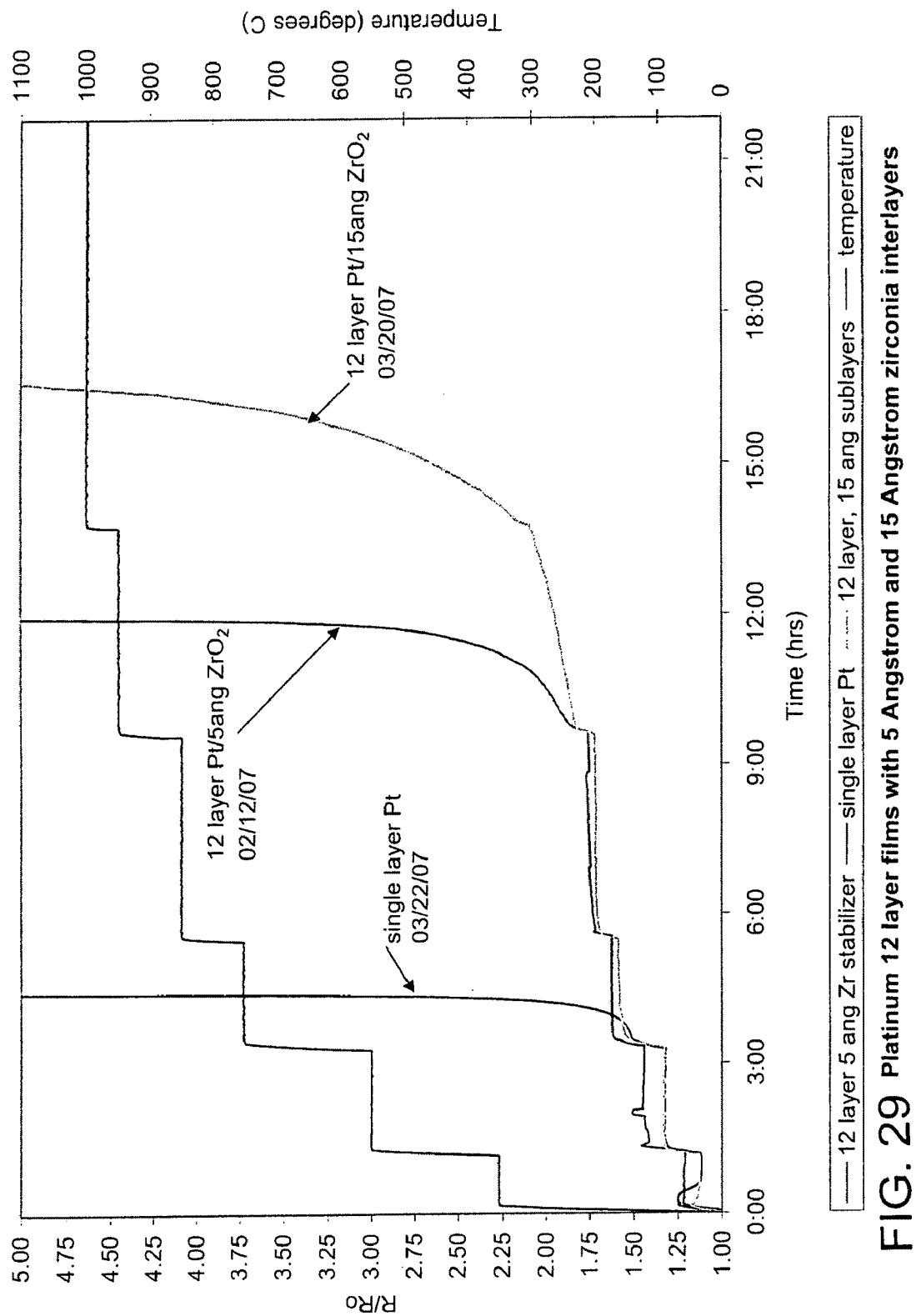
FIG. 29 Platinum 12 layer films with 5 Angstrom and 15 Angstrom zirconia interlayers

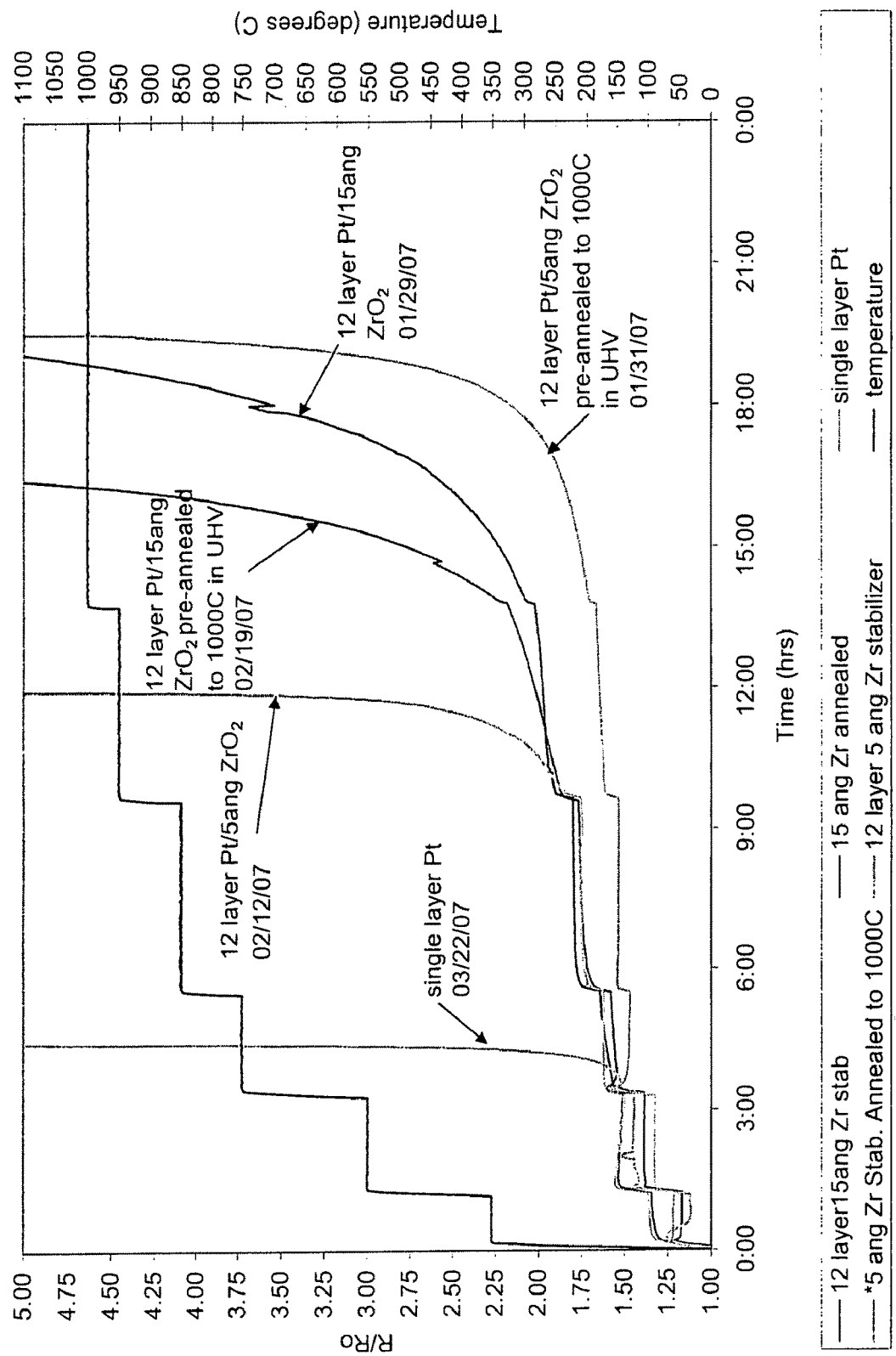
FIG. 30 Comparison of Pt 12-layer films with and without vacuum pre-anneal.

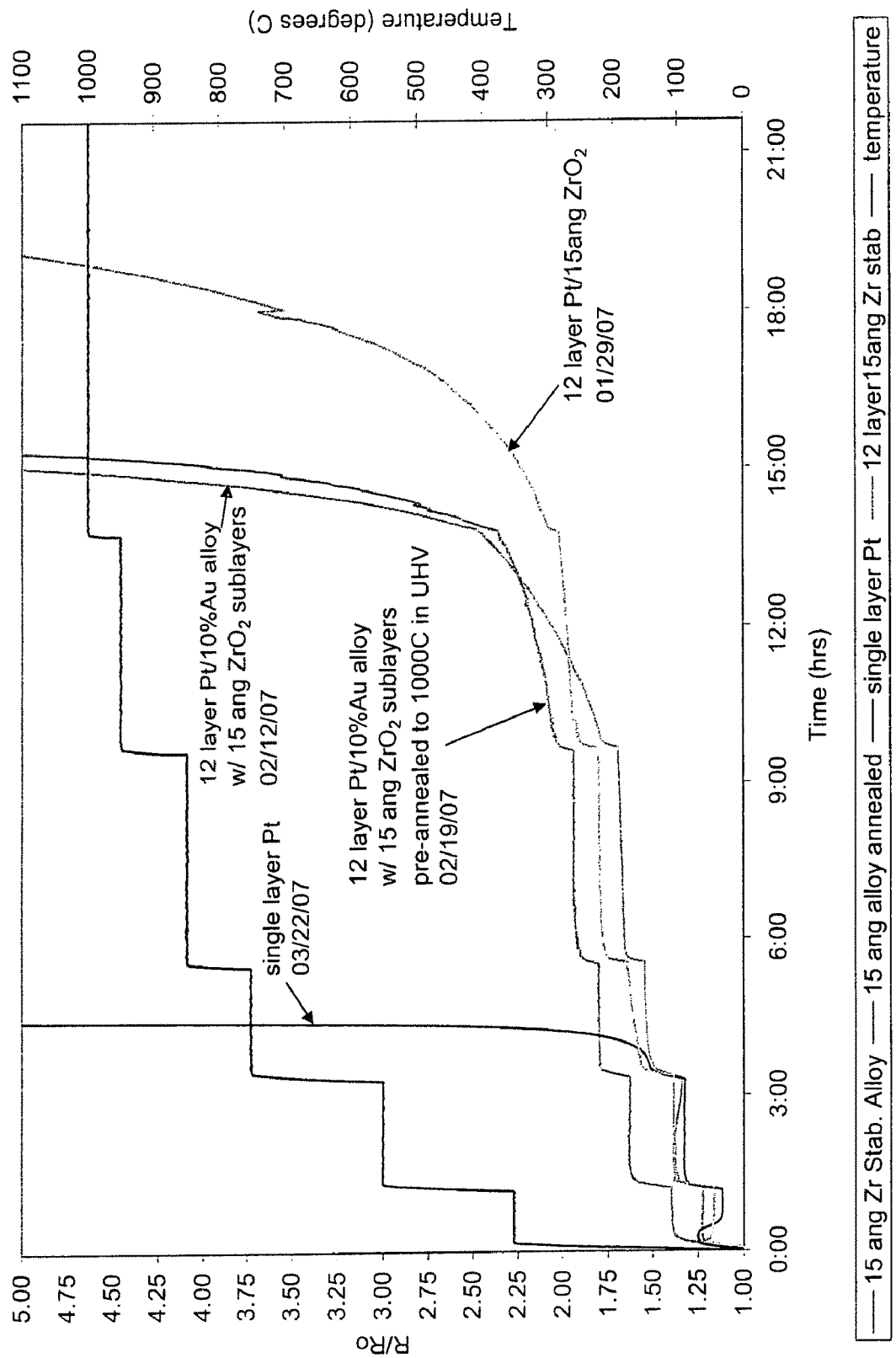
FIG. 31 Comparison of Pt and Pt/10%Au alloy 12-layer films.

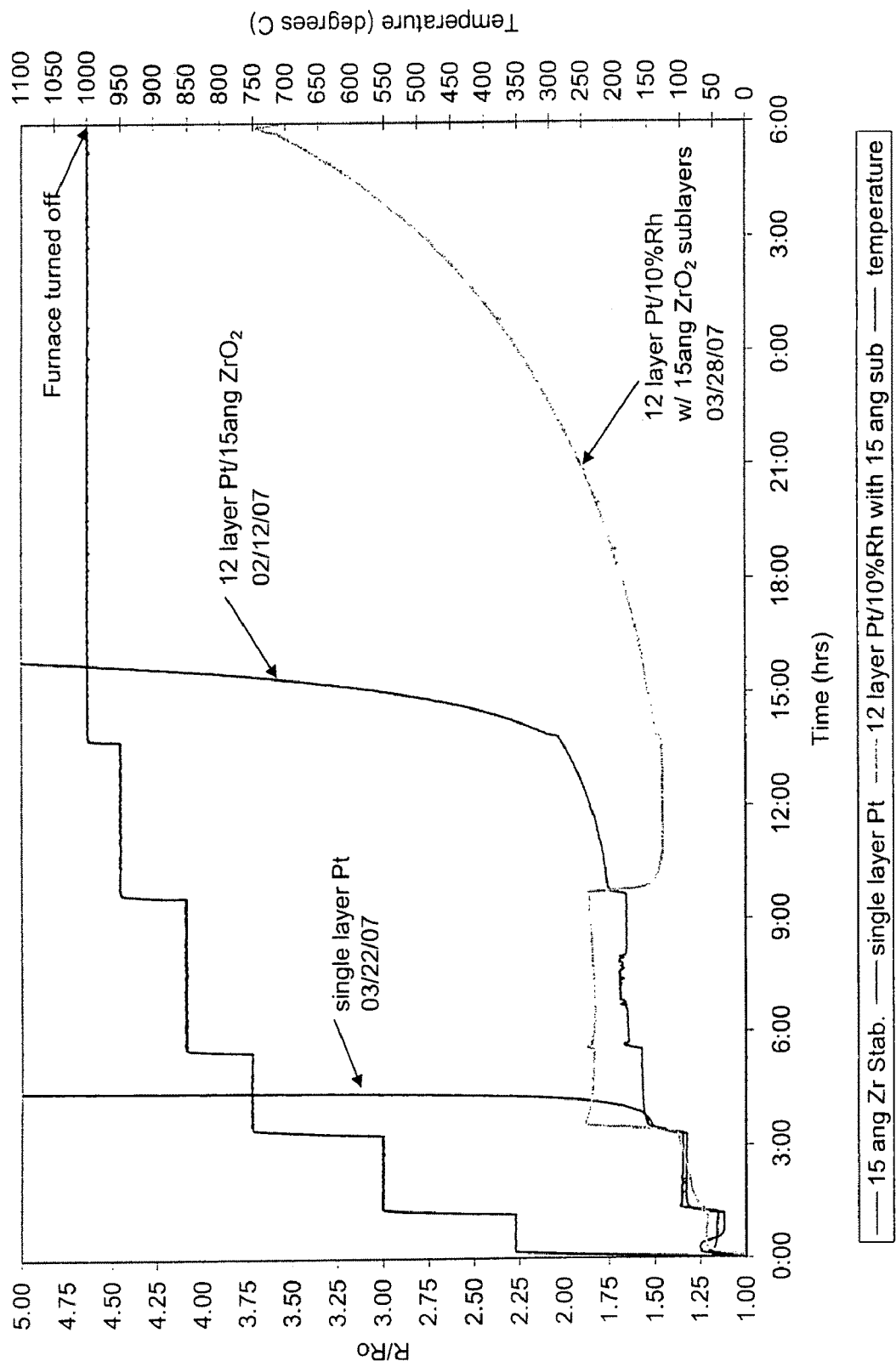
FIG. 32 Comparison of Pt and Pt-Rh alloy 12 layer films.

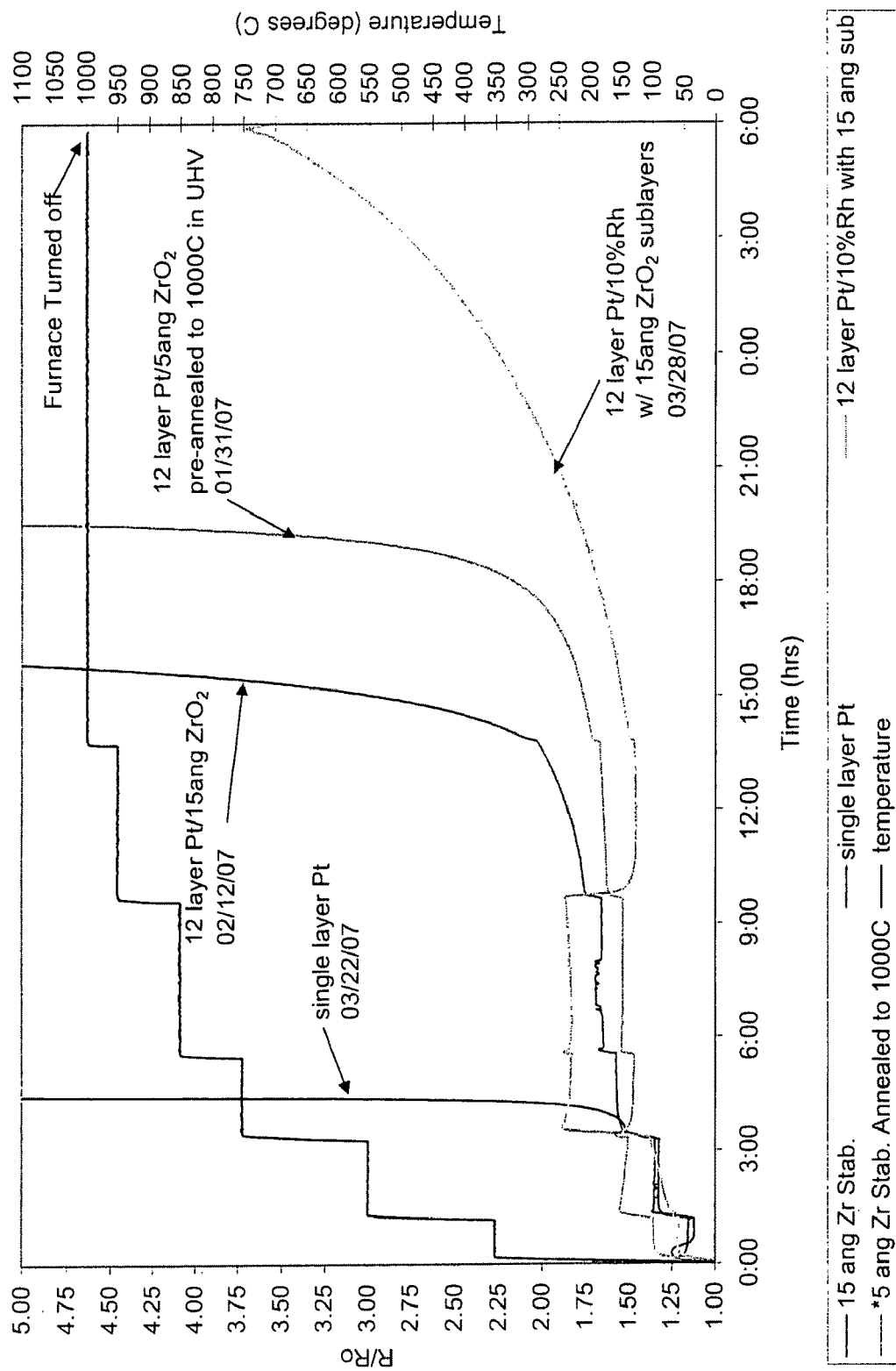
FIG. 33 Overall comparison of the best performing 12-layer films.

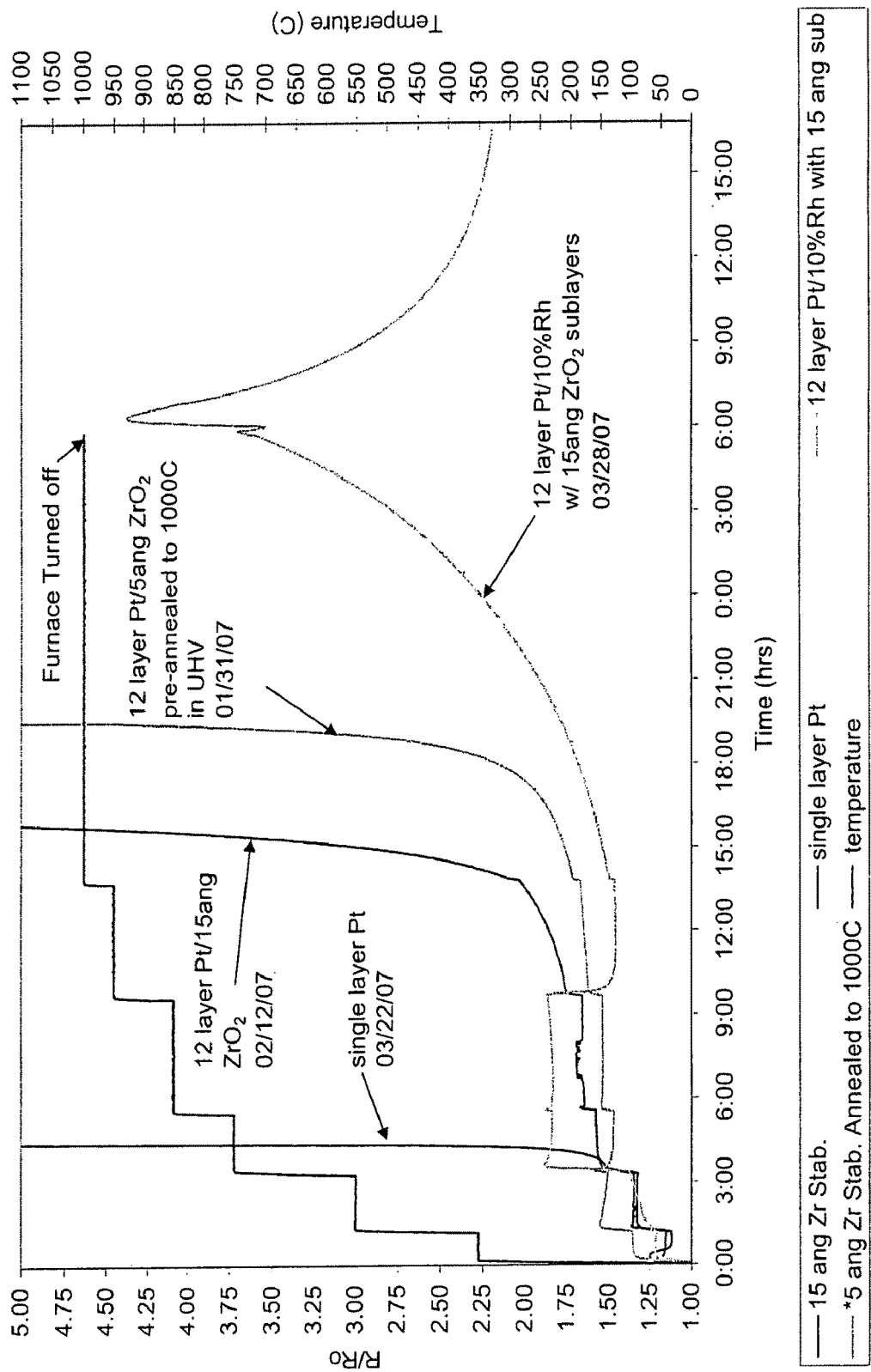
FIG. 34 Pt-Rh 12-layer film heated for 16 hours at 1000C followed by cooling to room temperature.

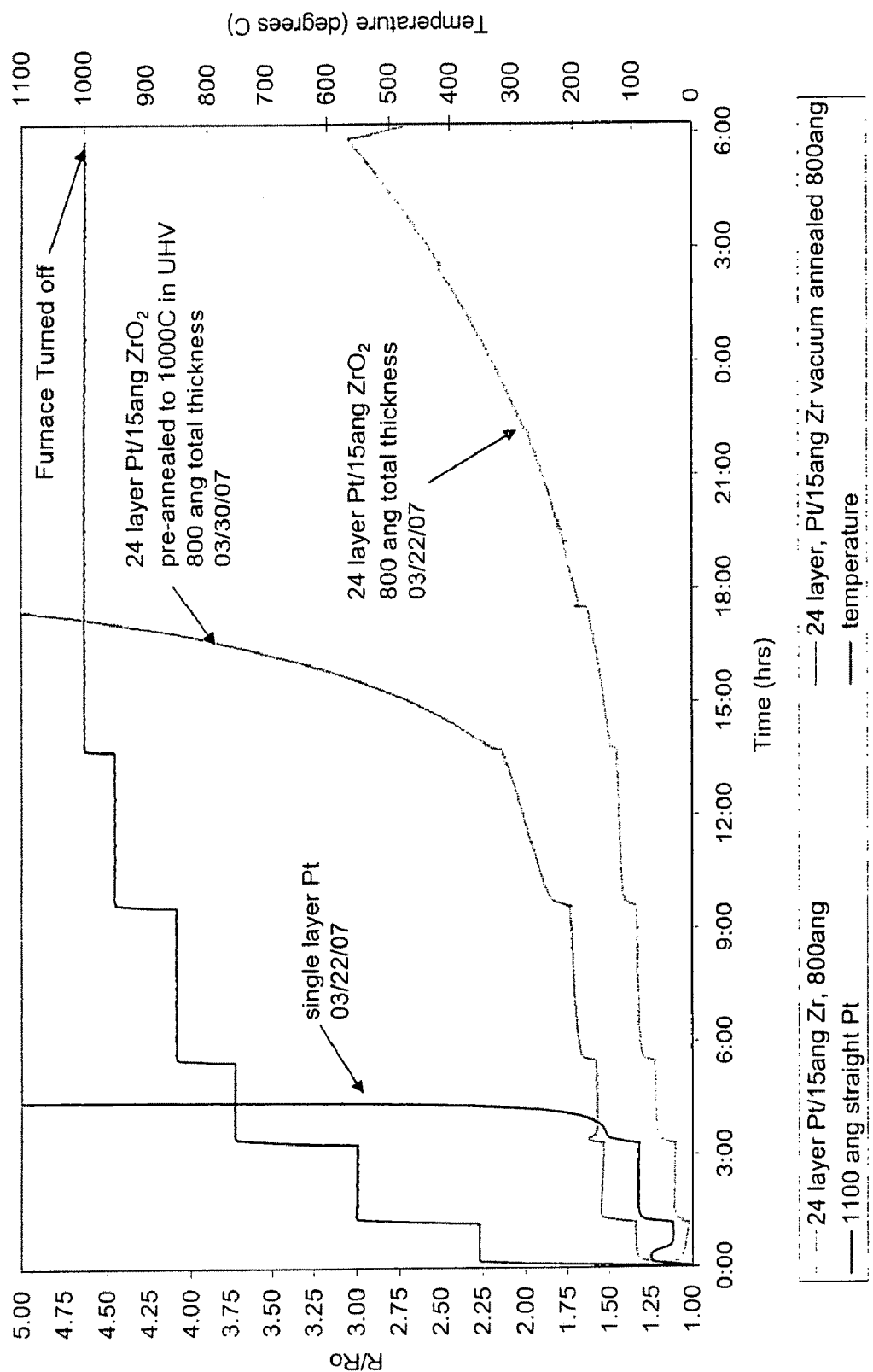
FIG. 35 24 layer Pt film with and without vacuum pre-anneal.

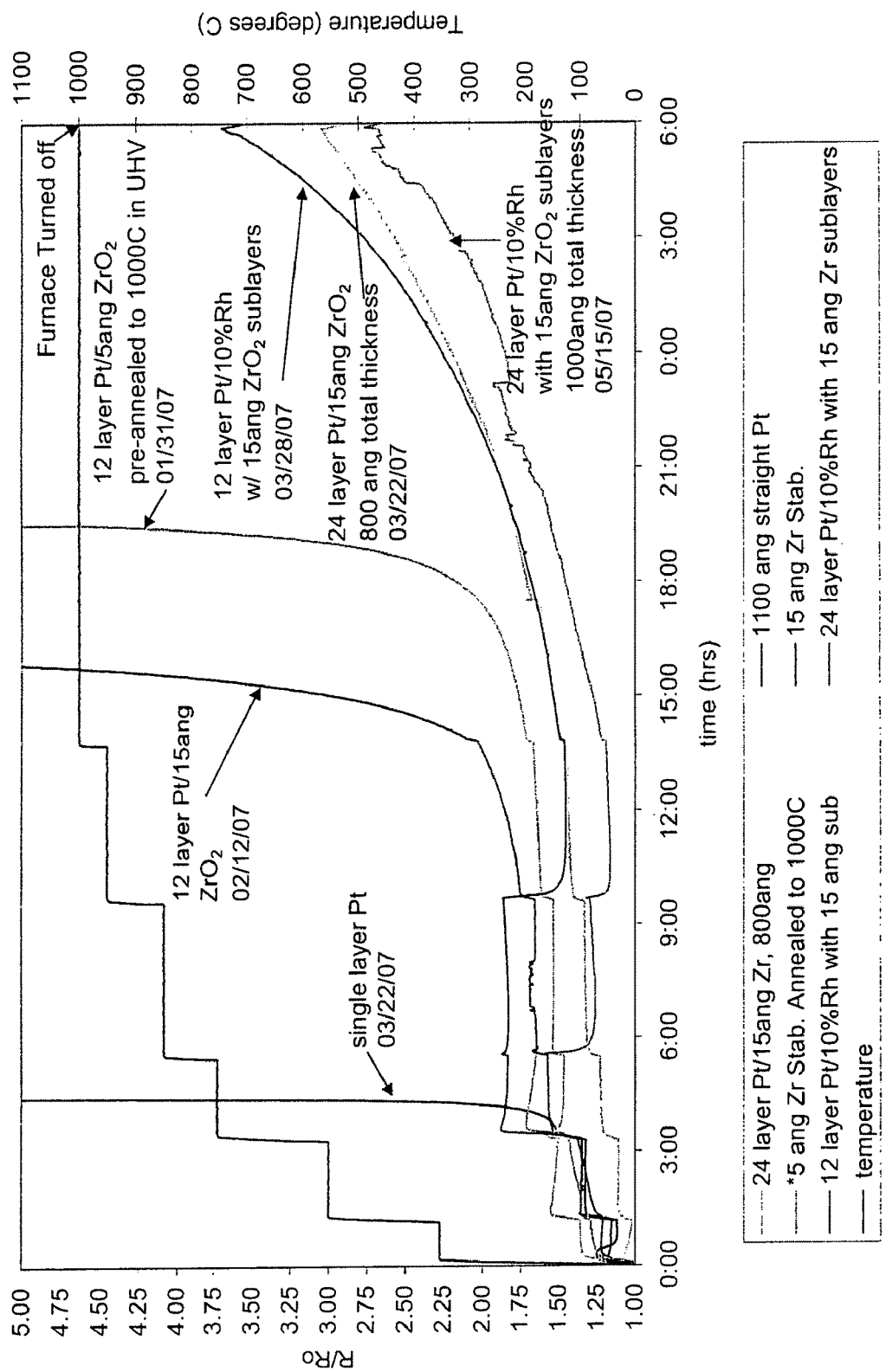
FIG. 36 Comparison of 12-layer and 24-layer films

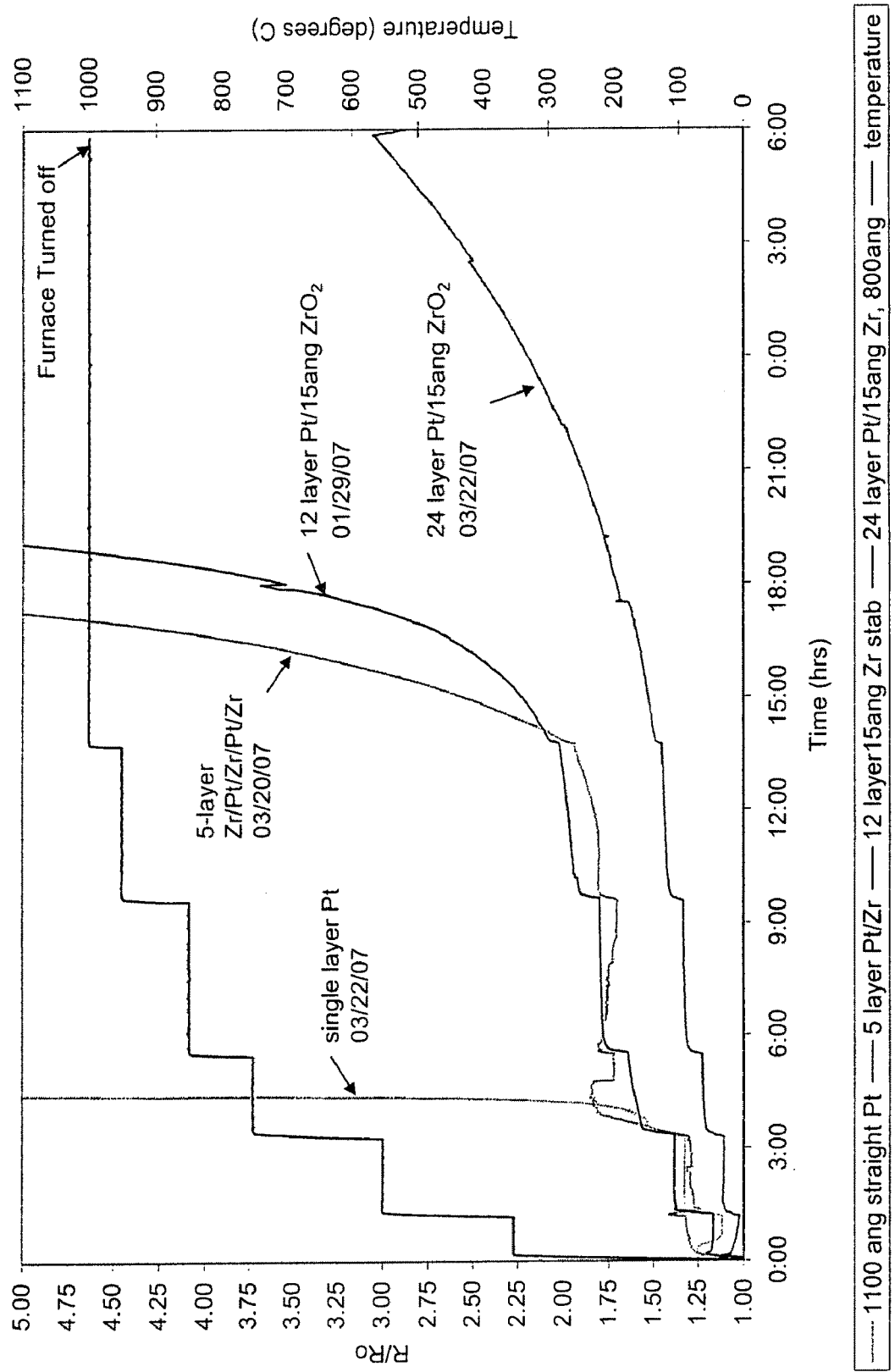
FIG. 37 Effect of layer structure on the performance of Pt films.

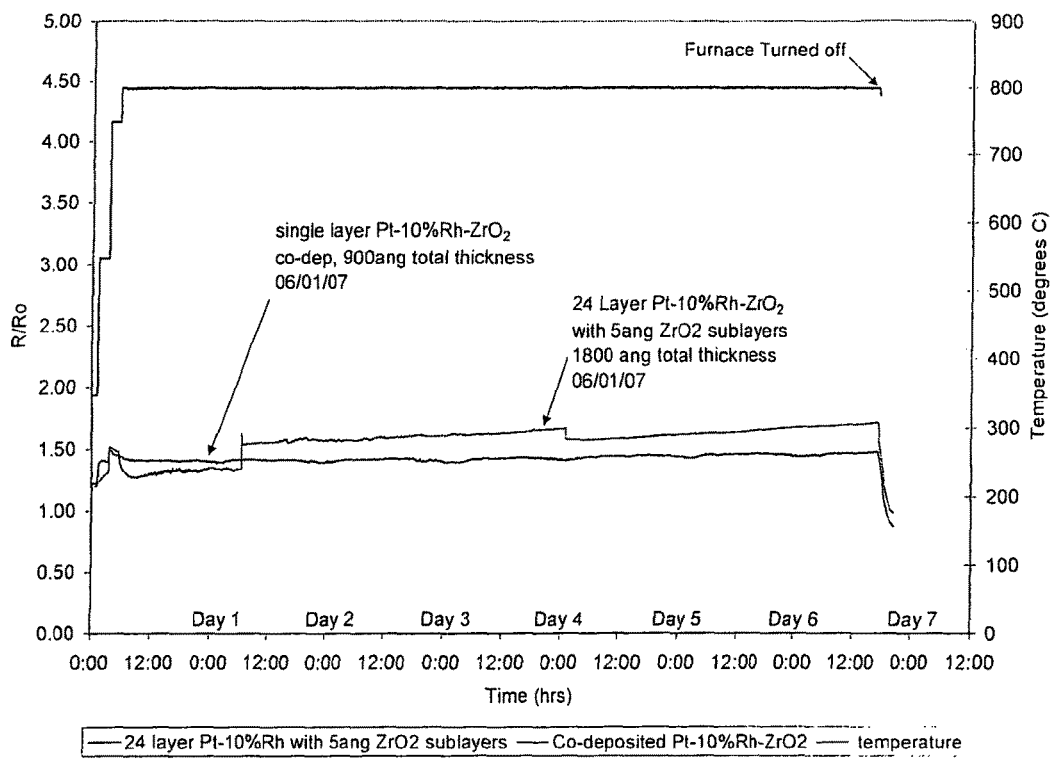
Fig 38 – Long Term High Temperature Test to 800°C with a co-deposited Pt-Rh-ZrO₂
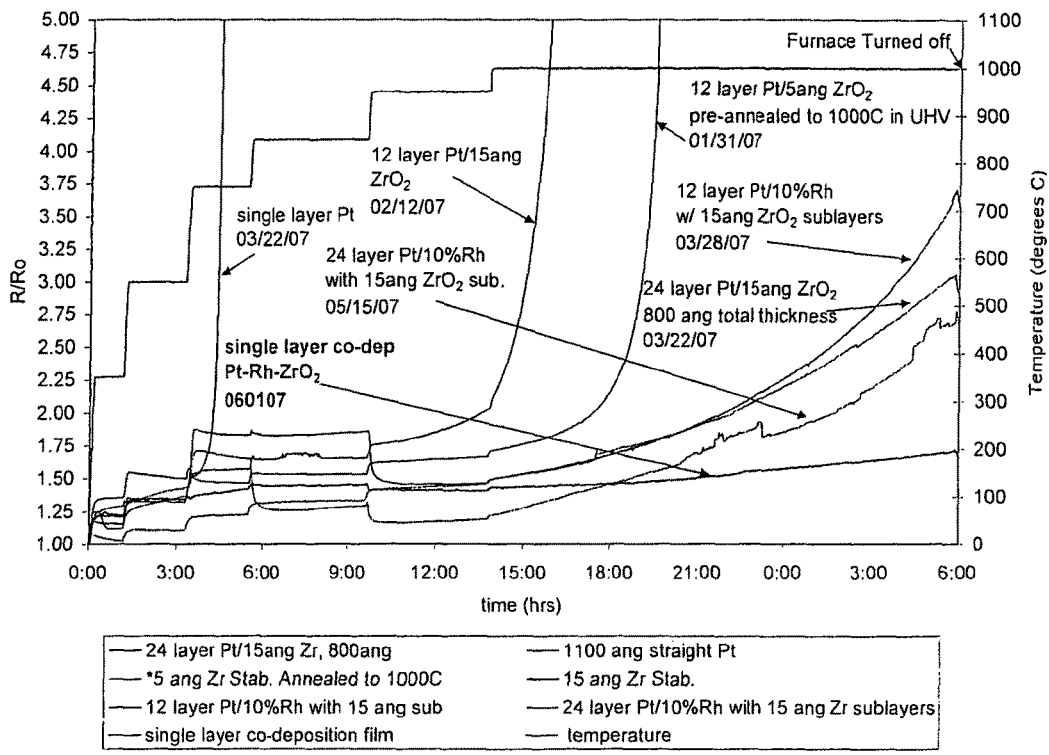
Fig 39 – Overall Comparison of Best Performing Films

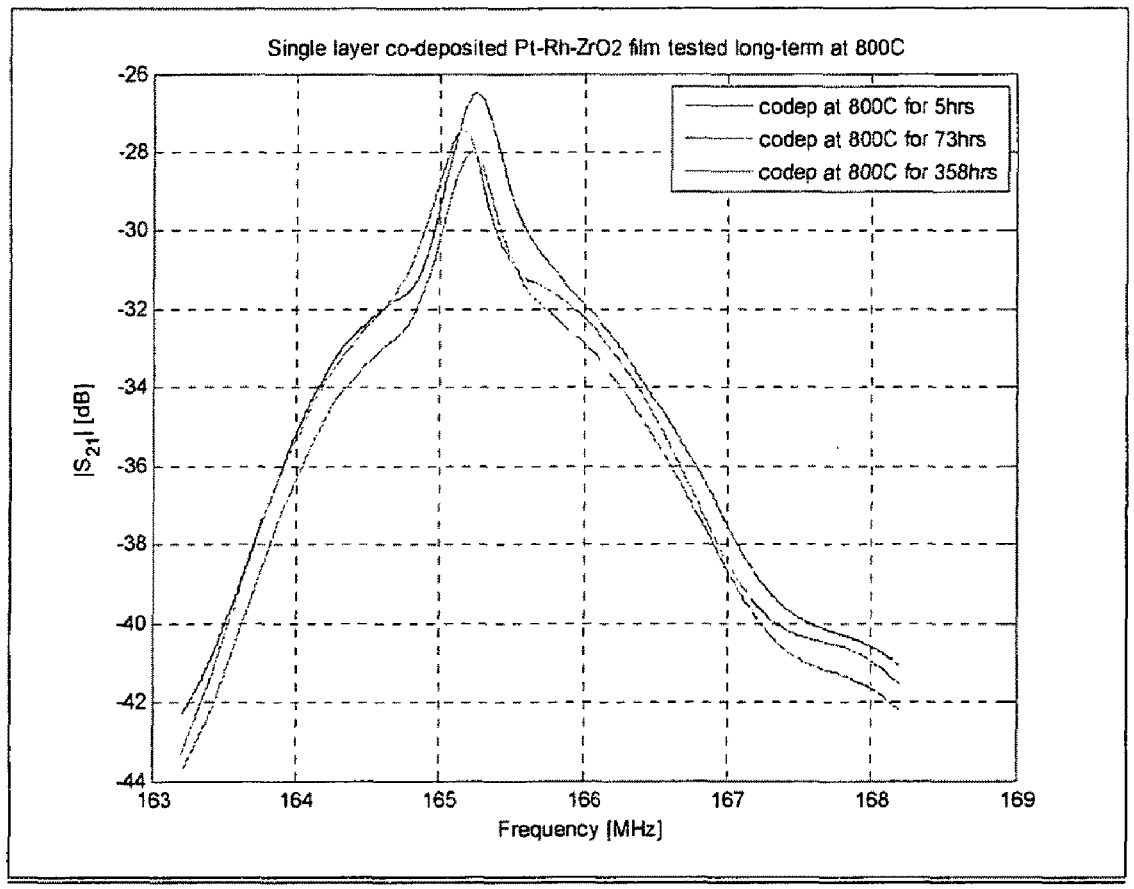
Fig 40 – High temperature LGS SAW resonator fabricated with Pt-Rh-ZrO2 co-deposited single film, operating at 800°C for over 360 hours.

ULTRA-THIN FILM ELECTRODES AND PROTECTIVE LAYER FOR HIGH TEMPERATURE DEVICE APPLICATIONS

CROSS-REFERENCE TO RELATED APPLICATIONS

This application is a continuation-in-part of U.S. patent application Ser. No. 11/046,712, filed Jan. 31, 2005, now U.S. Pat. No. 7,285,894, which claims priority from U.S. Provisional Application No. 60/544,650, filed Feb. 13, 2004. The disclosures of both applications are incorporated herein by reference.

STATEMENT REGARDING FEDERALLY SPONSORED RESEARCH OR DEVELOPMENT

Partial funding for this project was provided by National Science Foundation Grant No. ECS-0134335, Army Research Office ARO Grant #DAAD19-03-1-0117, Air Force Research Laboratory USAF Grant #FA8650-06-C-5209, Air Force Office of Scientific Research AFOSR Grant #F49620-02-1-0323 and Petroleum Research Fund ACS PRF#42747-AC10.

BACKGROUND OF THE INVENTION

This invention relates in general to high temperature devices and in particular to ultra-thin electrodes for surface acoustic wave devices and other semiconductor based devices for use in high temperature environments, vacuum or gases.

Surface Acoustic Wave (SAW) devices are electronic components that generate guided acoustic waves along a surface of the device. As the acoustic waves propagate along the surface of the device, any changes to the characteristics of the propagation path affect the velocity, and/or the delay, and/or the amplitude of the surface wave. Changes in the wave velocity, delay, or amplitude can be monitored by directly monitoring changes in the frequency, phase, or amplitude of the transmission or reflection electrical response of the device. The changes in frequency, phase, and/or amplitude are then correlated to a physical measured quantity, such as temperature, pressure, strain, stress, acceleration, or the detection of the presence of a specific gas. Thus, the device may be used as a sensor. Additionally, SAW devices also may be used as delay lines and resonators in electronic systems, for instance as frequency control devices in oscillator systems, which may be required to operate in harsh environments such as exposure to high temperature gases, high temperature corrosive environments, gas and oil wells, and industrial environments.

SAW sensors are among the most sensitive and widely used physical and chemical sensors in liquid and gas environments because the propagating acoustic wave has its energy concentrated close to the device surface. Along an arbitrary surface wave propagation direction, a particle in the substrate material describes an elliptical trajectory, with displacement components normal and parallel to the device surface. For liquid sensor applications, any SAW device operational mode with a significant particle displacement component normal to the surface suffers severe attenuation, thus compromising the device performance. However, this is less of a concern for gas sensor applications, since gases generally do not excessively absorb the wave energy. Accordingly, a regular, or generalized, SAW operational mode may be used for gas sensor applications.

SAW devices are typically fabricated on single crystal anisotropic substrates that are also piezoelectric, such as quartz. A piezoelectric material produces electrical charges when the material is subjected to stress. Furthermore, the phenomenon is reversible. A SAW device used as a sensor to measure temperature, pressure, or the presence of a gas, typically includes a pair of spaced apart intertwined aluminum interdigital electrodes disposed upon the surface of the substrate. Each of the interdigital electrode sets forms a transducer. One of the transducers creates mechanical stress within the substrate by applying an electric field to the crystal. The electric field is oscillatory to create a mechanical wave. Thus, the transducer converts the electrical signals applied to the device into the electromechanical surface acoustic waves that propagate along the surface of the substrate. The other transducer converts the received mechanical wave back into an electric signal for comparison to the original signal.

As an example of the application of SAW devices, one of the changeable characteristics of the propagation path is the temperature of the surrounding medium, which may be either gas or liquid in nature. The surface wave velocity, which is determined by the type of crystalline material, the selected the orientation, or cut, and the propagation direction used to fabricate the sensor, is temperature dependent. Thus, it is possible to correlate the SAW device change in surface wave velocity and material expansion along that orientation to the ambient temperature of the gases or liquids surrounding the device.

High temperature gas sensors are of interest for the aerospace industry as a safety tool for detection of fuel leaks in jet engines, early fire detection and detection of a hostile environment. High temperature gas sensors also are needed to increase combustion efficiency of jet engines, thereby reducing travel costs and air pollution due to unburned jet fuel. While Surface Acoustic Wave (SAW) devices have been successfully used in the past to measure gas temperatures, quartz, a widely used substrate for such devices, undergoes an $\alpha$ to $\beta$ phase transition at about 570° C. and loses its piezoelectric properties. Additionally, aluminum, the most commonly used material to form the interdigital transducers for a SAW device becomes soft when the temperature exceeds a few hundred degrees Centigrade and actually melts at 660° C. Thus, it is apparent that known SAW temperature sensors are limited in their temperature range and cannot be utilized to measure high temperatures, such as temperatures in excess of a few hundred degrees Centigrade. Accordingly, it would be desirable to provide a SAW sensor that could be operated at temperatures that are well above a few hundred degrees Centigrade.

BRIEF SUMMARY OF THE INVENTION

This invention relates to ultra-thin electrodes for surface acoustic wave devices and other semiconductor based devices for use in high temperature environments, vacuum or gases.

The present invention contemplates an ultra-thin film electrode including an electrically conductive layer formed from a material having an excellent thermal stability and a high melting temperature that is disposed upon an adhesive layer that is carried by a substrate. The invention also contemplates that the electrically conductive layer may include at least two layers formed from an electrically conductive material having an excellent thermal stability and a high melting temperature and further wherein each two of said layers of electrically conductive material have an interstitial layer that includes zirconium disposed there between. A protective layer that includes Silicon Aluminum Oxynitride (SiAlON) may be deposited over the conductive layer. Alternately, the conductive layer may be formed from a single layer of electrically conductive material having an excellent thermal stability and a high melting temperature. The electrically conducting material is selected from the group of platinum, palladium, an alloy of platinum, an alloy of palladium, rhodium or iridium. Alternately, the conducting material may be composite layer of platinum-rhodium and zirconium formed by depositing a platinum-rhodium alloy simultaneously with zirconium upon said adhesive layer in an atmosphere containing oxygen.

The present invention also contemplates utilizing the ultra-thin film electrode in a high temperature SAW delay line that includes a substrate formed from a material selected from the LGX family of crystals or gallium phosphate and having a SAW propagation surface. A first interdigital transducer is formed upon the substrate propagation surface from an electrically conductive material having a high melting temperature. The first transducer is operative to launch surface acoustic waves across the propagation surface. The sensor also includes a second interdigital transducer formed upon the substrate propagation surface from an electrically conductive material having a high melting temperature. The second transducer is spaced apart from the first interdigital transducer and is operative to detect the surface acoustic waves launched from the first interdigital transducer. In the preferred embodiment, LGS is used to form the substrate while the interdigital transducers are formed from platinum, or a platinum alloy or palladium in a single layer or in a layered configuration with interspersed layers of zirconia or from platinum or a platinum alloy co-deposited with zirconia or a combination of the above. The device also includes a protective ceramic SiAlON layer on top of the entire device or on top of selective areas of the device. The protective SiAlON layer has multiple purposes, which include: mechanical protection for the SAW device surface; improvement in the high temperature performance of the metallic electrodes deposited on the surface, by retarding the formation of Pt agglomeration, and therefore increasing the SAW device's high temperature operation limit; and finally for temperature compensated operation of the SAW device, since the temperature dependence of the SiAlON compensates the temperature behavior of the LGS SAW device. The sensor includes an adhesive layer that consists of zirconium disposed between the substrate and the interdigital transducers. Additionally, the invention contemplates depositing a film of material that is absorptive of a specific gas over the propagation surface and transducers to form a high temperature gas sensor.

The present invention further contemplates utilizing the ultra-thin film electrode in a resonator SAW device that includes two sets of reflecting electrodes formed upon the substrate with each set of reflecting strips, or electrodes, being between each of the interdigital transducers and the end of the substrate adjacent to said interdigital transducer. In the preferred embodiment, the reflecting electrodes are formed from platinum or palladium or a platinum alloy in a single layer or in a layered configuration with interspersed layers of zirconia or from platinum or a platinum alloy co-deposited with zirconia or a combination of the above. The device also includes a protective ceramic SiAlON layer on top of the entire device or on top of selective areas of the device. The protective SiAlON layer has multiple purposes, which include: mechanical protection for the SAW device surface; improvement in the high temperature performance of the metallic electrodes deposited on the surface, by retarding the formation of Pt agglomeration, and therefore increasing the SAW device's high temperature operation limit; and finally for temperature compensated operation of the SAW device, since the temperature dependence of the SiAlON compensates the temperature behavior of the LGS SAW device. The sensor also includes a zirconium adhesion layer disposed between the substrate and the reflecting electrodes. In the preferred embodiment, the ends of the reflecting electrodes are electrically connected by shorting bars; however, the invention also may be practiced without the shorting bars. Furthermore, the device may be fabricated as a one port resonator that includes a single interdigital transducer disposed between the two sets of reflecting electrodes. Additionally, the invention contemplates depositing a film of material that is absorptive of a specific gas over the propagation surface and transducer to form a high temperature gas sensor.

The invention additionally contemplates a method of fabricating the SAW delay line that includes providing a substrate formed from the LGX family of crystals or gallium phosphate. The substrate is cut to form a SAW propagation surface that is defined by a set of Euler angles. An adhesive layer of Zirconium is disposed upon the propagation surface. Then first and second interdigital transducers formed from an electrically conductive material having a high melting temperature are disposed upon the propagation surface of the substrate over the adhesive layer with the second interdigital transducer spaced apart from the first interdigital transducer. Additionally, a two port resonator may be formed by also disposing two sets of reflecting electrodes upon the adhesive layer with each set of reflecting electrodes being between one of the interdigital transducers and the end of the substrate adjacent to said interdigital transducer. Alternately, a one port resonator may be formed by disposing one interdigital transducer and two sets of reflecting electrodes upon the substrate with each set of reflecting electrodes formed upon the substrate between the interdigital transducer and one of the ends of the substrate.

Various objects and advantages of this invention will become apparent to those skilled in the art from the following detailed description of the preferred embodiment, when read in light of the accompanying drawings.

BRIEF DESCRIPTION OF THE DRAWINGS

FIG. 16 is a graph of experimental results obtained from high temperature testing of the three layer electrode film shown in FIG. 15.

FIG. 29 is a graph of experimental results obtained from high temperature testing of the electrode film shown in FIG. 27.

FIG. 30 is a graph illustrating the effect of annealing the electrode film shown in FIG. 27.

FIG. 31 is a graph of experimental results obtained from high temperature testing of a twelve layer electrode film that includes layers formed from an alloy.

FIG. 32 is a graph of experimental results obtained from high temperature testing of a twelve layer electrode film that includes layers formed from another alloy.

FIG. 33 is a graph comparing experimental results obtained from high temperature testing of a plurality of twelve layer electrode films.

FIG. 34 is a graph of experimental results obtained from high temperature testing of a twelve layer electrode film that includes layers formed from another alloy.

FIG. 35 a graph illustrating the effect of annealing the electrode film shown in FIG. 28.

FIG. 36 is a graph comparing experimental results obtained from high temperature testing of the 12 and 24 layer electrode film shown in FIGS. 27 and 28.

FIG. 37 is a graph comparing experimental results obtained from high temperature testing of electrode film having different numbers of layers.

FIG. 38 is a graph comparing the experimental performance of a single layer Pt-10% Rh and $ZrO_2$ co-deposited film with a 24 layer Pt-10% Rh and $ZrO_2$ film at 800° C. for one week. The test reveals superior performance of the co-deposited film with respect to the layered one.

FIG. 39 is a graph comparing experimental results obtained from high temperature testing of electrode films having different numbers of layers, including the Pt-10% Rh and ZrO2 co-deposited film.

FIG. 40 is a graph comparing experimental results obtained from high temperature testing of a high temperature LGS SAW resonator.

DETAILED DESCRIPTION OF THE PREFERRED EMBODIMENT

Figure 1:
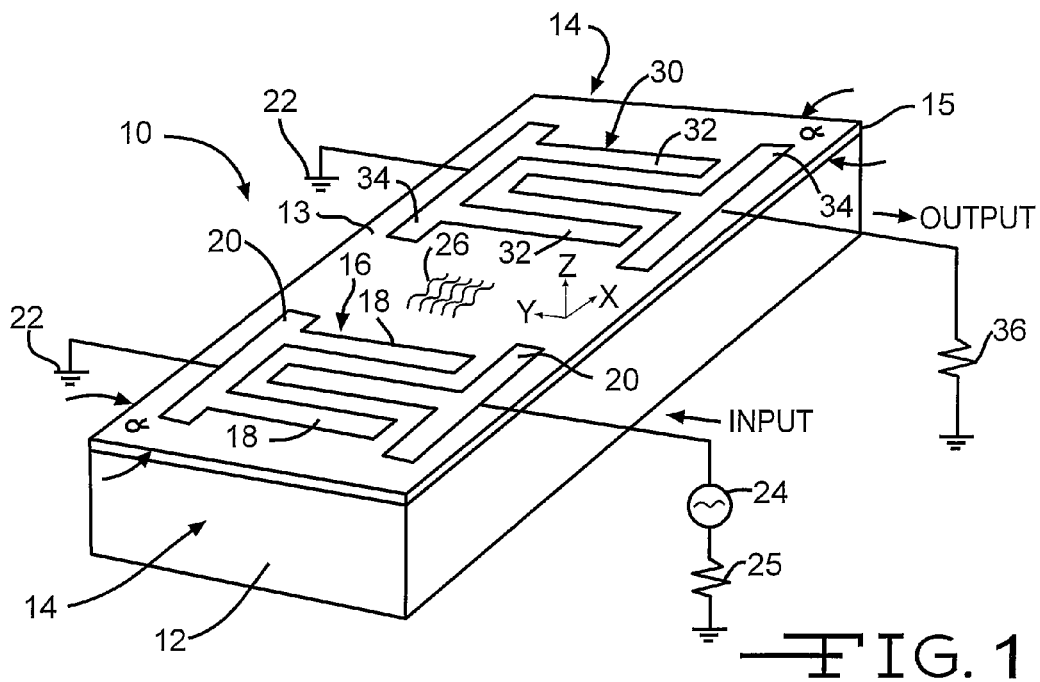
FIG. 1 is a perspective view of a Surface Acoustic Wave delay line device in accordance with the invention that is connected to an unbalanced generator and an unbalanced load.

Referring now to the drawings, there is illustrated in FIG. 1, a SAW device 10 for a high temperature application that is in accordance with the invention. The device 10 includes a substrate 12 formed from a crystal selected from the LGX family of crystals. The substrate 12 includes an upper surface 13 across which SAW propagate. The LGX family of crystals are materials of the trigonal crystal class 32, which is the same crystal class as quartz. The LGX family of crystals includes langatate (LGT, $La_3Ga_{5.5}Ta_{0.5}O_{14}$), langasite (LGS, $La_3Ga_5SiO_{14}$), langanite (LGN, $La_3Ga_{5.5}Nb_{0.5}O_{14}$), and variations, such as LGTS ($La_3 Ga_{5.25}Ta_{0.25}Si_{0.5}O_{14}$) and LGZS ($La_3Ga_5Zr_{0.5}Si_{0.5}O_{14}$). In the preferred embodiment, langasite, LGS, is used for the substrate 12. Additionally, the invention also contemplates using gallium phosphate ($GaPO_4$) for the substrate.

Figure 2:
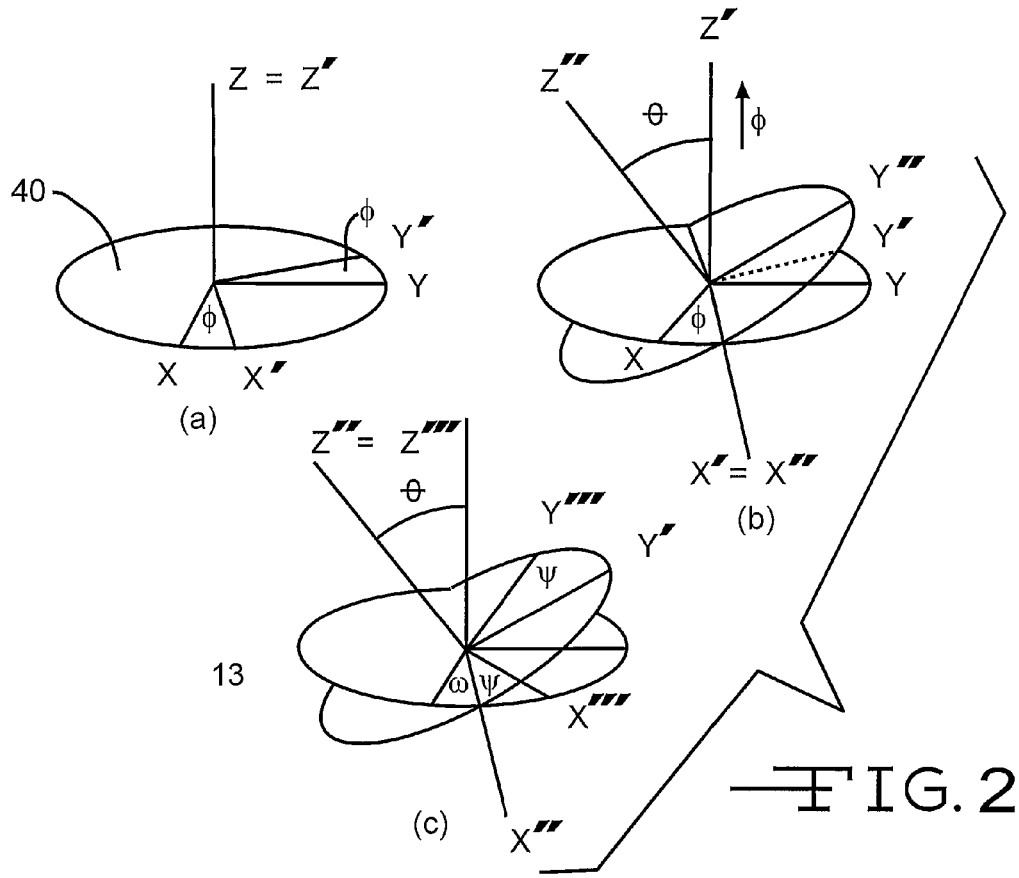
FIG. 2 illustrates the Euler angles that describe the orientation of the rotated substrate crystal axes of the device shown in FIG. 1 and the direction of SAW propagation on the device with respect to the non-rotated crystalline axes.

As described above, the material thermal expansion and the surface wave velocities are temperature dependent and are determined by the orientation, or cut, of the crystalline material used to fabricate the sensor. A set of Euler angles are used to define the cut of the crystalline material used to form the substrate 12. As illustrated in FIG. 2, the uncut LGS material is referenced by three orthogonal axes labeled X, Y and Z, while the surface 13 of the cut LGS material forming the SAW device substrate 12 is referenced by three orthogonal axes labeled X''', Y''' and Z'''. The elliptical surface labeled 40 in FIG. 2 that contains the axes X and Y represents the orientation of the crystals within the uncut LGS material, while the tipped elliptical surface that contains the axes X''' and Y''' represents the orientation of the crystals within the cut LGS material forming the substrate 12. Thus, the tipped surface has the same spatial orientation as the upper surface 13 of the SAW device substrate 12 and is therefore also labeled 13 in FIG. 2.

The spatial relationship between the two surfaces 40 and 13 are defined by first, second and third Euler angles, designated $\phi$, $\theta$ and $\psi$, respectively. The Euler angles represent rotations about the axes of the LGX material 40, to orient the axes, X''', Y''' and Z''', of the cut crystal surface 13. According to convention, the cut surface 13 is considered as being rotated first about the Z axis to offset the X' axis from the X axis by the first Euler angle $\phi$, as illustrated in FIG. 2(a). In FIG. 2(a) the other two axes are designated Y' and Z' following the first rotation. A second rotation then occurs about the X' axis by the second Euler angle $\theta$ to offset the Z'' axis from the Z' axis, as illustrated in FIG. 2(b). In FIG. 2(b), the other two axes are designated X'' and Y'' following the second rotation. Finally, the crystal is rotated about the Z'' axis to offset the X''' axis from the X'' axis by the third Euler angle $\psi$, as shown in FIG. 2(c). In FIG. 2(c), the other two axes are designated Y''' and Z''' following the third rotation. Thus, rotated axis Z''' is perpendicular to the surface 13 of the cut LGX crystals.

Use of the Euler angles ($\phi$, $\theta$, $\psi$) defines a unique substrate orientation. The inventor has determined that a regular SAW mode can be generated upon a crystal selected from the LGX family cut to have a crystal orientation that falls within specific ranges of the Euler angles is appropriate for a SAW device for use in high temperature gas applications. The specific Euler angle ranges include an Euler angle $\phi$ being within a range from $-20°$ to $+20°$; an Euler angle $\theta$, within a range from $0°$ to $+180°$; and an Euler angle $\psi$, within a range from $0°$ to $+90°$. High temperature gas sensors have been successfully fabricated by the inventor having Euler angles of ($0°$, $138.5°$, $26.6°$).

As shown in FIG. 1, each of the ends 14 of the substrate is beveled to form an acute angle, which is labeled $\alpha$, with one of the substrate sides. The beveled ends 14 avoid coherent reflection of SAW's from the substrate ends. However, depending upon the application of the SAW device 10, the beveled ends 14 may be omitted. For low temperature applications, the ends are not beveled, but a strip of wax, silicone rubber, epoxy or photo-resist may be utilized to prevent reflections of the waves.

A thin adhesion layer 15 of zirconium (Zr) is deposited upon the upper surface 13 of the substrate 12. Zirconium is selected over other common alternatives, such as Titanium (Ti), because Zr does not migrate into the electrode material, which would seriously compromise the SAW device performance during operation at high temperatures while also shortening the lifetime of the device. While Zr was used in the preferred embodiment, the invention contemplates that other non-migrating materials also may be utilized for the adhesion layer. In the preferred embodiment, the adhesion layer 15 has a thickness of 40 Å; however, the invention also may be practiced with greater or lesser thickness of the adhesion layer.

As shown in FIG. 1, an input Interdigital Transducer (IDT) 16 is fabricated upon the adhesion layer 15 from an electrically conductive material that has a high melting temperature. The input IDT 16 includes interdigital electrodes having a plurality of intertwined fingers 18. The electrode fingers 18 are perpendicular to axis X''' and parallel to axis Y'''. In the preferred embodiment, the IDT 16 is formed from platinum (Pt) because the material has a high melting temperature of 1769° C. Because platinum has a high density, almost eight times that of aluminum, a platinum film having a thickness of 500 Å is applied. However, it will be appreciated that the invention also may be practiced with greater or lesser thickness of the Pt forming the IDT 16 than 500 Å. Alternately, the preferred embodiment may use palladium (Pd), which has a melting temperature of 1554.9° C., to form the electrodes of the IDT 16. In the preferred embodiment, palladium having a thickness of 3000 Å is applied to the adhesion layer 15. Again, the invention also may be practiced with greater or lesser thickness of the Pd forming the IDT 16 than 3000 Å.

The input IDT 16 is of conventional design and, in the preferred embodiment, has 80 intertwined fingers 18 that are each 4 micrometers wide and a 1:1 mark-to-space ratio. However, the invention also may be practiced with other numbers of fingers and with other finger sizes and spacing for the input IDT 16. For example, the electrode finger width is typically a function of the operating frequency for the device 10. The input transducer 16 also includes a first pair of busbars 20 with each busbar 20 connecting ends of the electrode fingers 18. The busbars 20 provide the capability to electrically connect the input transducer 16 to other electrical components and thus function as terminals for the device 10. While the input IDT 16 is shown with the electrode fingers 18 extending from one of the busbars 20 alternating with the electrode fingers extending from the other busbar, it will be appreciated that the IDT also may include other patterns for the electrode fingers. For example, two or more electrode fingers may extend from one of the busbars between two adjacent electrode fingers extending from the other busbar (not shown).

Figure 3:
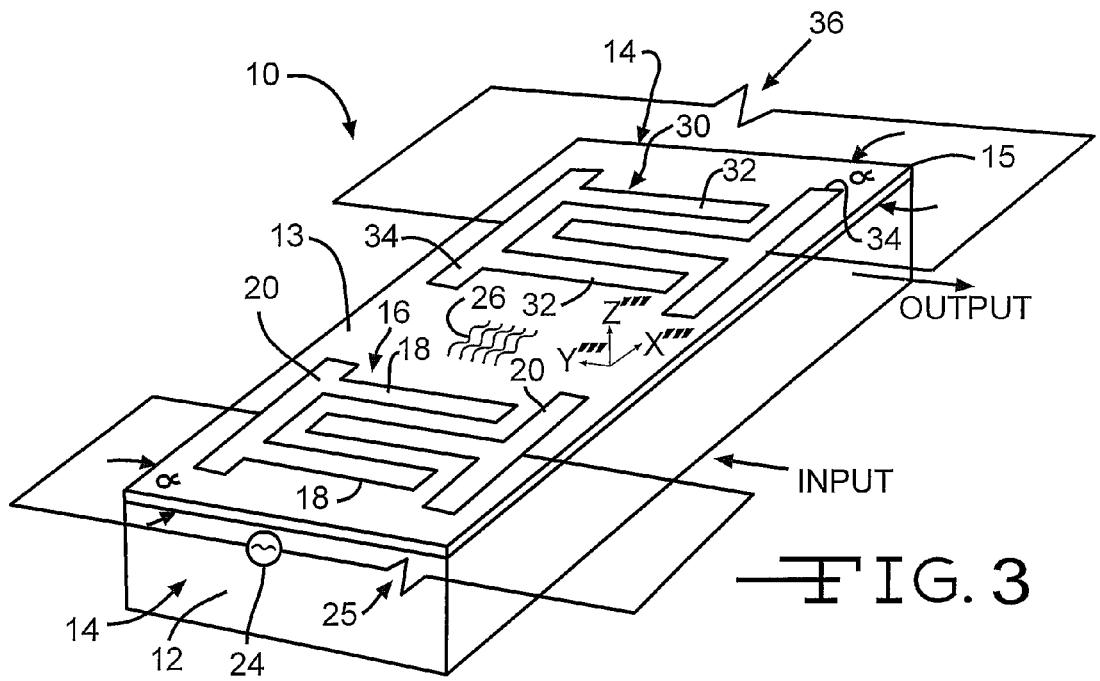
FIG. 3 is a perspective view of the Surface Acoustic Wave delay line device shown in FIG. 1 that is connected to a balanced generator and a balanced load.

As illustrated in FIG. 1, one of the busbars 20 is connected to electrical ground 22 while the other busbar is connected to an electrical component, such as, for example an oscillator 24 and an oscillator internal impedance 25, resulting in an unbalanced connection. Alternately, the oscillator 24 and oscillator internal impedance 25 may be connected across the input IDT busbars 20, as illustrated in FIG. 3, resulting in a balanced, or floating, connection. The input transducer 16 is responsive to excitation by the oscillator 24 to generate surface acoustic waves that propagate across the upper surface 13 of the substrate 12, as shown by the representative regular SAW labeled 26 in FIG. 1. The preferred embodiment of the invention utilizes a regular SAW, which also may be referred to as a generalized SAW, a Rayleigh SAW or an arbitrary symmetry SAW.

In the preferred embodiment, the input IDT 16 is formed by conventional thin film deposition methods and photolithography utilizing ultra-violet light. The method begins by carefully polishing the crystalline substrate surface 13. The method continues with either lift off or wet etch deposition of the input IDT 16 and other metallic structures upon the surface 13 of the substrate 12. In the preferred embodiment, lift off deposition is used; however, wet etch deposition also may be used. With lift off deposition, photo-resist is applied with spin coating over the entire polished substrate surface. The photo-resist is then baked. A mask is placed over the photo-resist and the substrate is exposed to ultraviolet light. If positive photo-resist is used, the mask includes opaque areas that correspond to areas on the substrate surface that are not to be metalized. The areas of photo-resist exposed to the ultraviolet light undergo a chemical reaction that allows them to be subsequently removed by a developing solution. After removing the exposed areas of photo-resist with the developing solution, the adhesion layer 15 is applied over the entire surface. The electrode metal is then deposited by a conventional method, such as vacuum metalization, over the entire adhesion layer 15. Finally, the remaining photo-resist is removed, or lifted off, from the substrate surface 13. As the remaining photo-resist is removed, the adhesion layer and electrode metal covering the photo-resist also is removed, leaving the pattern of metal that defines the input interdigital transducer 16 and other structures. If a negative photo-resist is used, the areas of photo-resist exposed to the ultraviolet light remain while the unexposed areas are removed. Accordingly, the mask used with negative photo-resist is the inverse of the mask described above with the opaque areas corresponding to the areas to be metalized. The unexposed areas of photo-resist are removed with the developing solution and the method continues as described above.

With wet etch deposition, the layer of adhesion layer is applied directly over the entire polished substrate surface and then the electrode metal is deposited over the adhesion layer. The substrate is then spin coated with photo-resist which is cured by baking. Portions of the metal coating that are to be removed are exposed through a mask to ultraviolet light. A mask is placed over the photo-resist and the substrate is exposed to ultraviolet light. If positive photo-resist is used, the mask includes opaque areas that correspond to areas on the substrate surface that are to be metalized. The areas of photo-resist exposed to the ultraviolet light undergo a chemical reaction that allows them to be subsequently removed by a developing solution. After removing the exposed areas of photo-resist with the developing solution, the substrate surface is chemically etched to remove the exposed areas of the electrode metal and adhesion layers. The remaining photo-resist prevents removal of the areas of the electrode metal and adhesion layers that are still covered. Finally, the remaining photo-resist is removed, leaving the pattern of metal that defines the input interdigital transducer 16 and other structures. If a negative photo-resist is used, the areas of photo-resist exposed to the ultraviolet light remain while the unexposed areas are removed. Accordingly, the mask used with negative photo-resist is the inverse of the mask described above with the opaque areas corresponding to the areas that are not to be metalized. The unexposed areas of photo-resist are removed with the developing solution and the method continues as described above.

For the SAW device 10 shown in FIG. 1, the surface acoustic waves propagate along the axis labeled X''' and are received by an output Interdigital Transducer (IDT) 30 that also is formed upon the upper surface 13 of the substrate 12 from an electrically conductive material that has a high melting temperature. In the preferred embodiment, the output IDT 30 is formed from platinum or a platinum alloy in a single layer, in a layered configuration with interspersed layers of zirconia, or from platinum or a platinum alloy co-deposited with zirconia or a combination of the above, by the same conventional thin film technology described above. Alternately, the preferred embodiment of the output IDT 30 may be formed from palladium. Similar to the input IDT 16, the output IDT 30 includes 80 interdigital electrodes having a plurality of intertwined fingers 32 that are each 4 micrometers wide and a 1:1 mark-to-space ratio. However, the invention also may be practiced with other numbers of fingers and with other finger sizes and spacing for the output IDT. For example, the electrode finger width is typically a function of the operating frequency for the device 10. The electrode fingers 32 are perpendicular to axis X''' and parallel to axis Y'''. The output transducer 30 also includes a second pair of busbars 34 with each busbar 34 connecting ends of the electrode fingers 32. The busbars 34 provide the capability to electrically connect the output transducer 30 to other electrical components. While the output IDT 30 is shown with the electrode fingers 32 extending from one of the busbars 34 alternating with the electrode fingers extending from the other busbar, it will be appreciated that the IDT also may include other patterns for the electrode fingers. For example, two or more of electrode fingers may extend from one of the busbars between two adjacent electrode fingers extending from the other busbar (not shown).

The SAW devices, either delay line or resonator, may also includes a protective ceramic SiAlON layer (300 Å, but could be more or less, depending on the application) on top of the entire device or on top of selective areas of the device. The protective SiAlON layer has multiple purpose, which include: mechanical protection for the SAW device surface; improvement in the high temperature performance of the metallic electrodes deposited on the surface, by retarding morphological changes, and therefore increasing the SAW device's high temperature operation limit; and finally for temperature compensated operation of the SAW device, since the temperature dependence of the SiAlON coating compensates the temperature behavior of the LGS SAW device.

As described above for the input IDT 16, one of the output IDT busbars 34 may be connected to electrical ground 22 while the other busbar is connected to an electrical component, such as, for example a load 36, as illustrated in FIG. 1, resulting in an unbalanced connection. Alternately, the load 36 can be connected across the output IDT 30 busbars 34, as illustrated in FIG. 3, resulting in a balanced, or floating, connection. The output IDT 30 is operative to convert the electromechanical SAW's back into an electrical signal. For the SAW device 10 shown in FIG. 1, the signal generated by the output IDT 18 is applied to the electrical load labeled 36.

As shown in FIG. 1, the device 10 is configured as a delay line with the output IDT 30 spaced apart from the input IDT 16. In the preferred embodiment, the input and output transducers 16 and 30 have an aperture distance, or the length of the overlapping portions of the electrode fingers, that is equivalent to 50 SAW wavelengths; however, other aperture distances may be used. Also, the centers of the IDTs 16 and 30 are separated along the direction of propagation by a distance that is equivalent to 350 SAW wavelengths; however, the invention also may be practiced having other distances separating output IDT 30 from the input IDT 18. The distance may be expressed in either wavelengths of in measured units of length. Thus, for example, the invention also contemplates that the centers of the IDTs 16 and 30 may be separated by a distance within a range of five to 3,000 wavelenths or a range of one mm to five cm.

Several significant improvements have been obtained with the present invention. The inventor has discovered that the SAW device 10 as shown in FIG. 1 and having platinum or palladium electrode fingers deposited upon a LGS substrate is capable of operating in high temperature environments, up to temperatures of about 750° C. The inventor also verified that the device 10 can be successfully operated at temperature well in excess of 800° C. with modifications to the conductive electrodes described below. A similar SAW sensor having platinum IDTs disposed directly upon a conventional quartz substrate (not shown) was also fabricated and tested in the same high temperature environment. The inventor found that an output signal no longer could be detected from the quartz sensor when it was exposed to temperatures in the 570-580° C. range. Additionally, irreversible loss of the piezoelectric effect was experienced for the quartz at 625° C. An Auger analysis and X-ray photoelectron spectroscopy of the quartz substrate revealed the migration of silicon from the quartz substrate into the platinum IDT film, after the device had been exposed to high temperatures for several hours. In contrast, the device 10 was successfully operated for over six months in a high temperature gaseous environment, an unexpected duration of operation.

Figure 4:
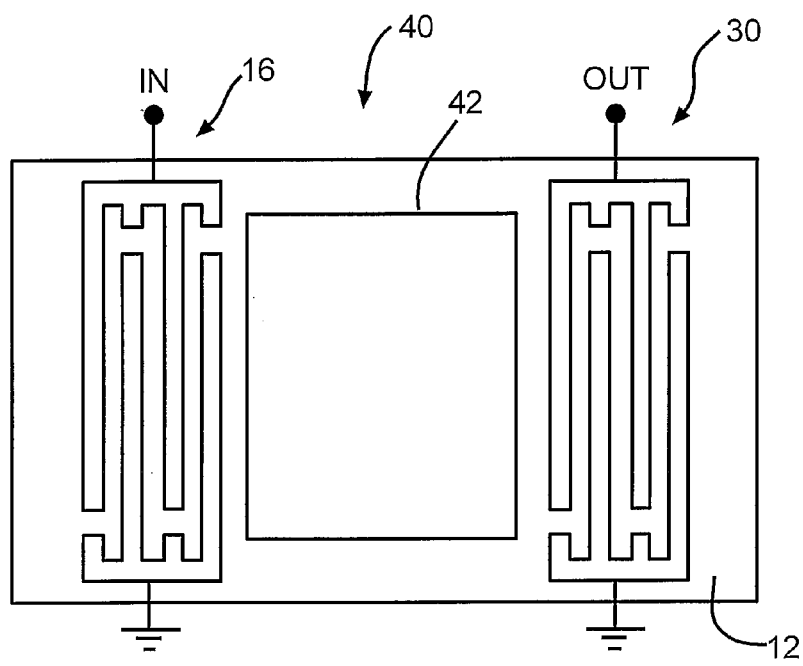
FIG. 4 is a plan view of an alternate embodiment of the Surface Acoustic Wave delay line shown in FIG. 1 that is intended for gas detection.

The delay line configuration shown in FIG. 1 may be used in high temperature and pressure sensors applications and within electronic equipment intended for use in a high temperature environment. The invention also contemplates modifying the delay line shown in FIG. 1 to function as a sensor. Such a sensor 40 is illustrated in FIG. 4 where components that are similar to components shown in FIG. 1 have the same numerical designators. As shown in FIG. 4, a thin film of material 42 that is absorptive of a specific gas is deposited upon the substrate surface 13 between the IDT's 16 and 30. When exposed to the gas, the sensing film 42 absorbs some of the specific gas and changes the propagation characteristics of the SAW's, such as the velocity of wave propagation. The change in wave propagation velocity is detected and indicative of the presence of the gas. Because of the materials, the device 40 may be used as a gas detector in high temperature environments, such as jet engine exhaust ports. As shown in FIG. 4, the ends of the substrate 12 are not beveled to form an acute angle with the sides of the substrate, as described above; however, the invention also may be practiced with substrate ends formed at an angle α to the sides, as shown in FIG. 1.

The invention also contemplates that, for several applications, the platinum, palladium, platinum alloy or a palladium, alloy films in a single layer, or in a layered configuration with interspersed layers of zirconia, or from platinum or a platinum alloy co-deposited with zirconia, or a combination of the above, forming the IDTs are sufficient for sensing the presence of a gas. Certain gases, such as, for example, $H_2$ are absorbed directly into the Pd IDT film and cause a change in the velocity of SAW propagation without the additional film 42 shown in FIG. 4. Also, as will be described in the following, the sensing film may be deposited over the entire upper surface of the substrate to include the IDTs 16 and 30.

Figure 5:
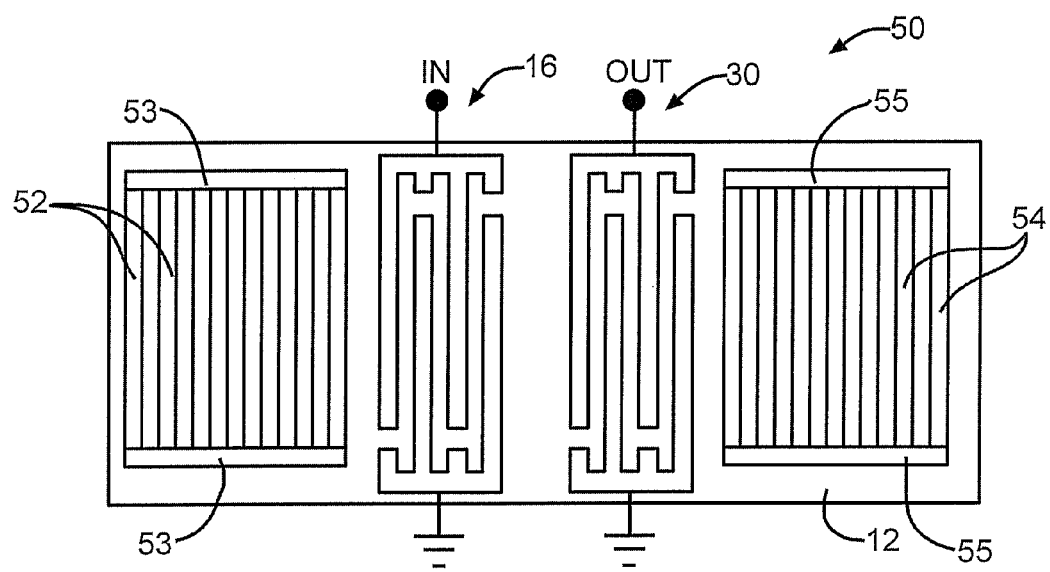
FIG. 5 is a plan view of a two port Surface Acoustic Wave resonator in accordance with the invention that includes shorted reflecting strips and is intended for gas detection.

The present invention also contemplates another embodiment shown generally at 50 in FIG. 5 where the device is configured as a two port resonator. Components shown in FIG. 5 that are similar to components shown in the previous figures again have the same numerical designators. The SAW device 50 includes a plurality of parallel reflector strips, or reflecting electrodes, 52 and 54 that extend transversely across the ends of the LGX substrate 12. The reflecting strips 52 and 54 are formed from the same electrically conductive material having a high melting temperature as the IDT's 16 and 30. In the preferred embodiment, there are 250 strips having a 500 Å thickness are formed upon each end of the substrate 12. However, it will be appreciated that the invention also may be practiced with greater or lesser thickness of the material forming the reflecting electrodes 52 and 54 than 500 Å. Also in the preferred embodiment, the reflector strips are each 4 micrometers wide and the reflector strips have a 1:1 mark-to-space ratio. Again, it will be appreciated that the invention also may be practiced with other numbers of, or sizes and spacing, for the reflecting electrodes 52 and 54. Additionally, the width of the individual reflecting electrodes used in the resonator may vary. The two port resonator 50 also includes a first pair of shorting bars 53 that electrically connect the ends of the reflecting strips 52 to the left of the drawing and a second pair of shorting bars 55 that electrically connect the ends of the reflecting strips 54 to the right of the drawing. The shorting bars 53 and 55 restrict the operation of the reflecting strips 52 and 54, respectively, by eliminating any electrically caused portion of the reflected SAW while modifying the response of the resonator 50. Thus, any reflections present in the resonator 50 are limited to mechanical, or mass loading, components of the SAW. As shown in FIG. 5, the ends of the substrate are not beveled, as described above; however, it may be useful to have the substrate ends formed at an acute angle α to the sides, as shown in FIG. 1, to avoid reflection of other modes at the border that could interfere with the main reflected mode. In the preferred embodiment, the reflector strips are formed from platinum or palladium by the same conventional thin film technology described above.

One of the busbars for each of the IDT's is typically electrically grounded while the other busbar is either the input terminal or output terminal for the device resulting in an unbalanced loading of the device 50. Alternately, a balanced connection (not shown), as described above, may be used with the device 50. The input IDT 16 generates a SAW that is reflected by the reflector strips 52 and 54 to generate a standing wave upon the propagation surface of the device 50. Thus, the device 50 functions as a resonator cavity at a resonance frequency determined by the configuration of the device. The output IDT 30 is used to sample the standing wave. The resonator device 50 is intended for use in high temperature environments as a filter or other frequency control device. By monitoring the shift in the frequency or phase response of the resonator device 50, the device also may be used to measure temperatures, pressures and/or gas presence and concentration.

Figure 6:
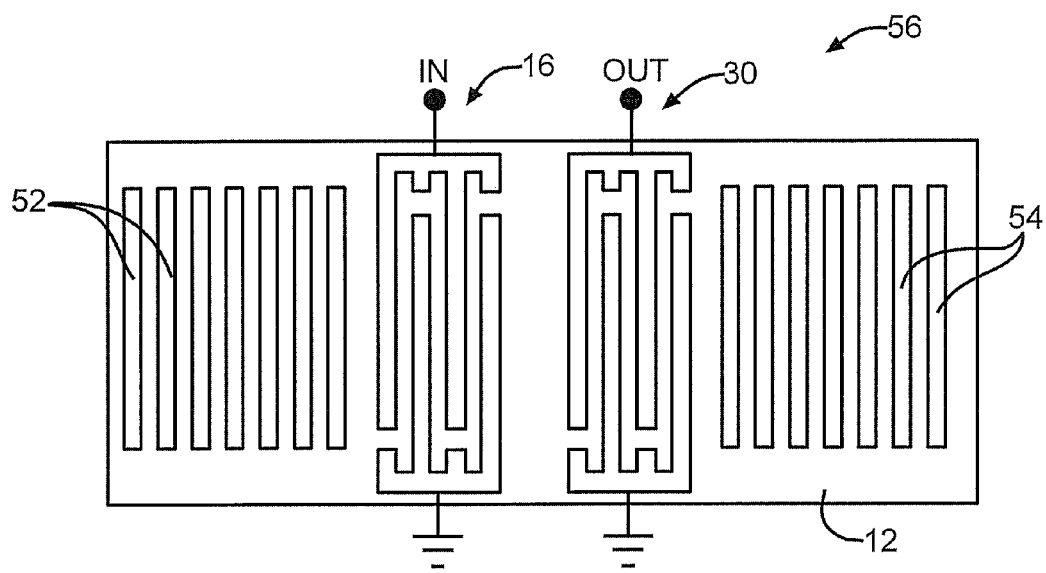
FIG. 6 is a plan view of an alternate embodiment of the resonator shown in FIG. 5 that includes open reflecting strips.

The invention also contemplates an alternate embodiment of the two port resonator 50 that is shown generally at 56 in FIG. 6, where components that are similar to components shown in the preceding drawings have the same numerical identifiers. The resonator 56 is similar to the resonator 50 described above, except that the shorting bars 53 and 55 have been omitted.

Figure 7:
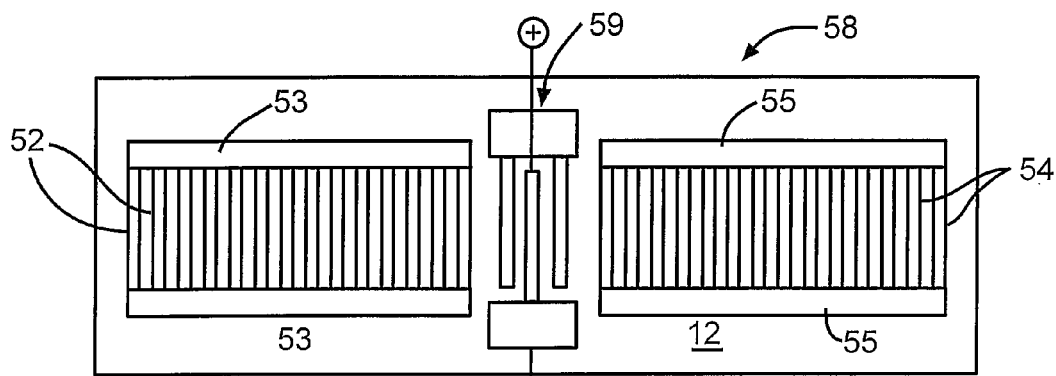
FIG. 7 is a plan view of an alternate embodiment of the resonator shown in FIG. 5 that has a single IDT.
Figure 7A:
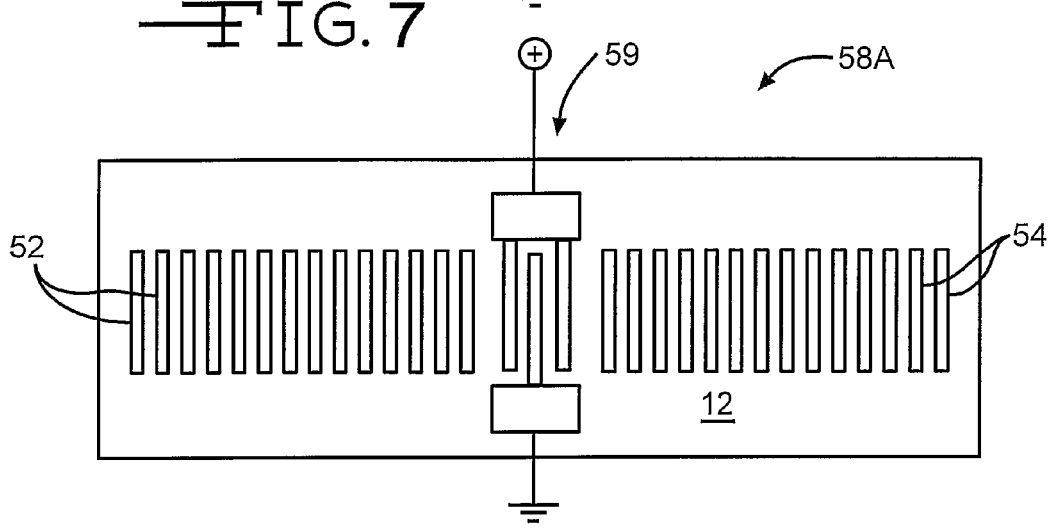
FIG. 7A is a plan view of an alternate embodiment of the resonator shown in FIG. 7.

Yet another embodiment of the resonator is shown generally at 58 in FIG. 7, where components that are similar to components shown in the preceding drawings again have the same numerical identifiers. The resonator 58 is a one port device having a single IDT 59 disposed between two sets of reflector strips 52 and 54. As shown in FIG. 7, the ends of each set of reflector strips 52 and 54 are electrically connected by pairs of shorting bars 53 and 55, respectively. Alternately, the shorting bars 53 and 55 may be omitted as shown for the one port resonator 58A illustrated in FIG. 7A. The single IDT 59 generates a SAW that is reflected by the reflector strips 52 and 54 to create a standing wave or a resonator cavity at the resonate frequency. While the resonance is the same as occurs in the two port resonators 50 and 56 described above, the single IDT 59 also is utilized to sample the resonating signal. Such one port resonators 58 may not only be used for sensor and frequency control functions, but also for filtering applications where several one port resonators may be utilized as a bandpass filter (not shown). While the preferred embodiment of a one port resonator is shown in FIG. 7, it will be appreciated that the invention also contemplates a one port resonator that does not include the shorting bars 53 and 55 (not shown).

As described above, the two port resonator SAW device 50 also can be used as a high temperature gas detection device. Such a gas detection device is illustrated generally at 60 in FIG. 8 where components that are similar to components shown in the preceding figures have the same numerical identifiers. The high temperature gas detector 60 includes a layer 62 of chemically sensitive material applied to the upper surface 13 of the substrate 12 and over the IDT's 16 and 30, the reflector strips 52 and 54 and the shorting bars 53 and 55. During operation of the gas sensor 60, the chemically sensitive layer 62 absorbs specific vapors from the surrounding air. The absorption changes the mass loading and the film parameters of the sensor 60 and thus has an effect upon the device's frequency response. The change in frequency response is correlated with the specific gas being detected. Because the sensor 60 is fabricated with heat tolerant materials, the sensor can be utilized to detect specific gases in a high temperature environment. Alternately, a biological film (not shown) can be deposited on the upper surface 13 of the substrate 12 and over the IDT's 16 and 30, the reflector strips 52 and 54 and the shorting bars 53 and 55 to enhance detection of biological agents present in the surrounding environment.

As described above, for certain gases, the platinum, palladium films, or platinum alloy films in a single layer, or in a layered configuration with interspersed layers of zirconia, or from platinum or a platinum alloy co-deposited with zirconia, or a combination of the above, forming the IDTs and reflector strips are sufficient for sensing the presence of a gas. In such cases, the chemically sensitive layer 62 may be omitted from the sensor (not shown). Additionally, the high temperature gas sensor 60 also may be configured as a one port resonator device (not shown), similar to the device shown in FIG. 7, but with chemically sensitive material applied to the upper surface 13 of the substrate 12 and over the single IDT 59, the reflector strips 52 and 54 and the shorting bars 53 and 55. While the preferred embodiment of the sensor 60 has been illustrated with pairs of shorting bars 53 and 55 connecting the ends of the reflector strips 52 and 54, respectively, it will be appreciated that invention also may practiced with the shorting bars 53 and 55 omitted (not shown).

Figure 9:
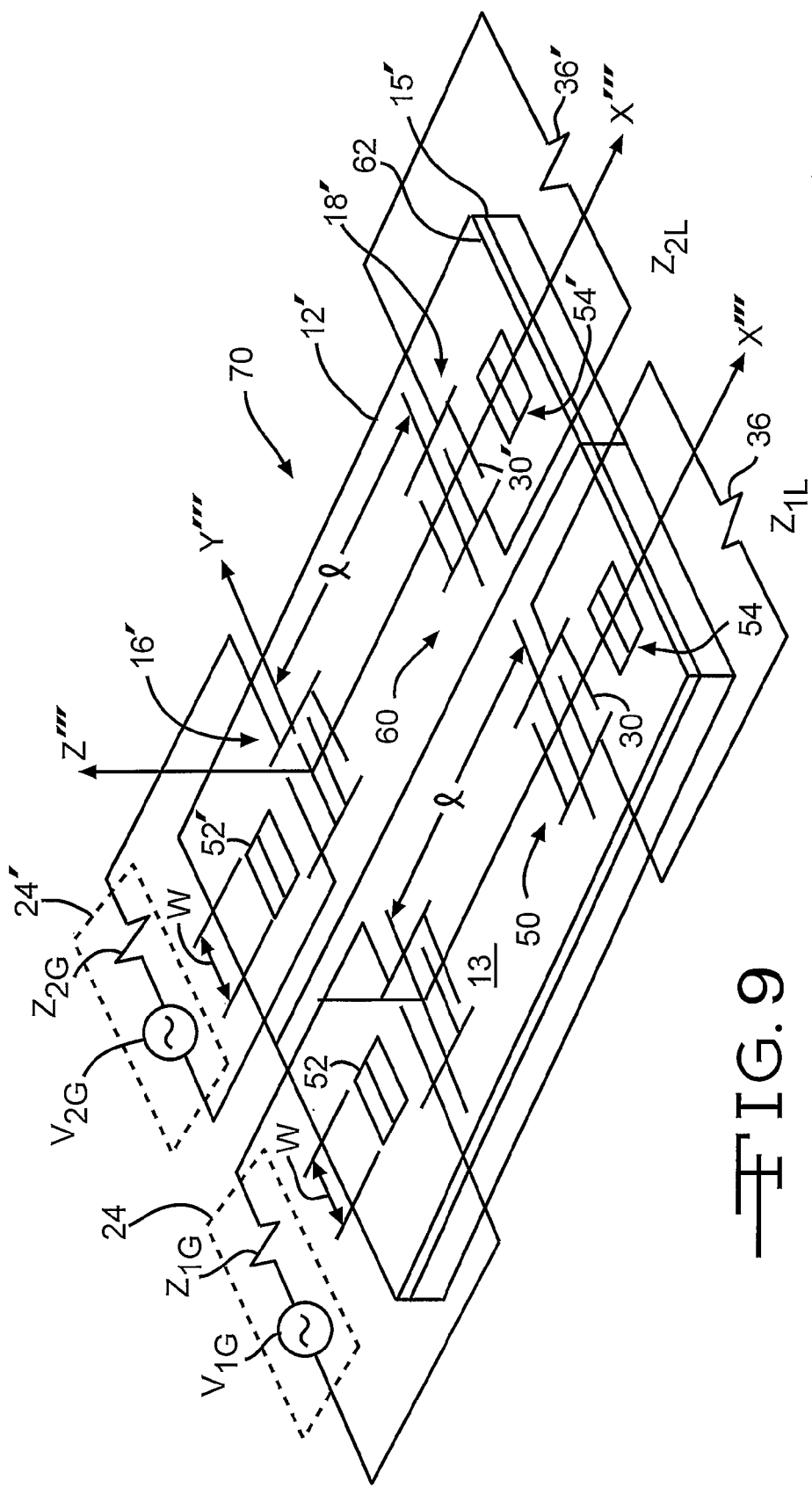
FIG. 9 is a perspective view of a combined Surface Acoustic Wave device that includes dual two port Surface Acoustic Wave resonators as shown in FIG. 8.

The invention also contemplates a combined sensor, shown generally at 70, in FIG. 9 that provides both temperature data and gas detection in a high temperature environment. Components shown in FIG. 9 that are similar to components shown in preceding figures have the same numerical identifiers. As shown in FIG. 9, a single substrate 14 carries a first Surface Acoustic Wave resonator 50 for measuring temperature and a second Surface Acoustic Wave resonator 60 with a surface coating 62 for detecting the presence of a specific chemical substance, such as, for example, a gas. The components of the second resonator 60 are identified with primes. Thus the sensor 70 provides dual functions. Additionally, the temperature data obtained from the temperature sensor 50 in FIG. 96 can be utilized for temperature compensation of the chemical detection data obtained from the upper sensor 60. While the preferred embodiment of the sensor 70 has been illustrated with pairs of shorting bars connecting the ends of the reflector strips, it will be appreciated that invention also may practiced with the shorting bars omitted (not shown). Additionally, the high temperature gas sensor 70 also may be configured utilizing a one port resonator device (not shown), similar to the device shown in FIG. 7. Similarly, the present invention contemplates utilizing a pair of delay lines deposited upon a single substrate (not shown). With dual delay lines, one delay line would be used to measure temperature while the other delay line, with a surface coating for detecting a chemical substance deposited between the IDT's, would be used to detect the presence of the chemical substance.

Experimental Results

Figure 10:
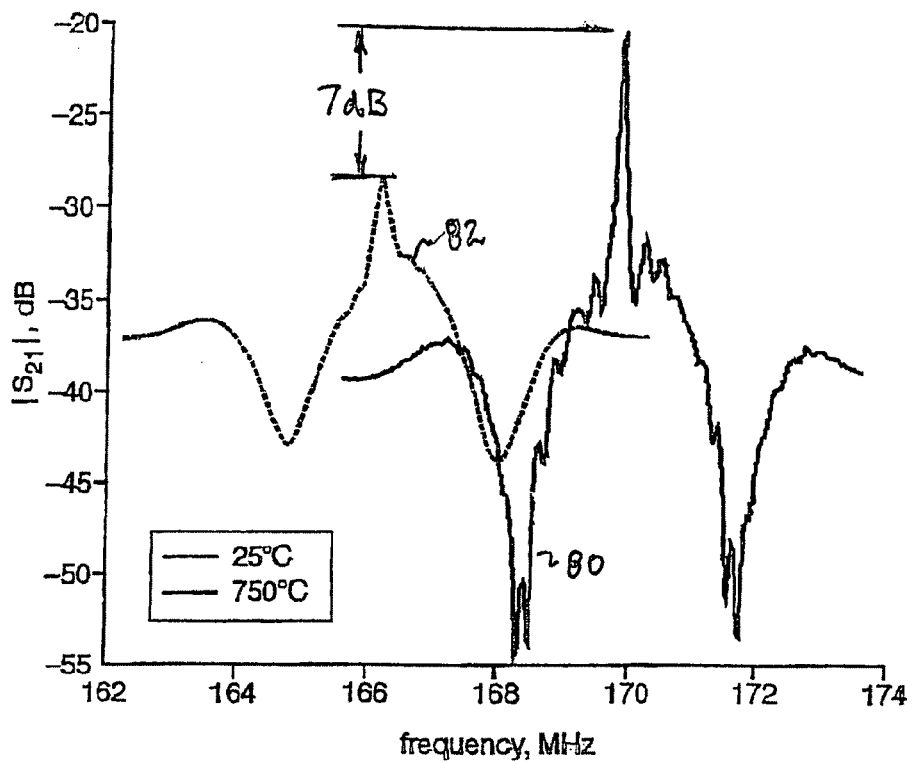
FIG. 10 is an experimentally obtained graph illustrating the frequency variation of the scattering parameter transmission coefficient amplitude, $|S_{21}|$, for a SAW device in accordance with the invention for two temperatures.

The frequency response of a two port SAW resonator fabricated with Pt transducers on Zr with an LGS substrate in accordance with the invention is illustrated by the frequency response curve shown in FIG. 10 where the transmission coefficient, $|S_{21}|$, which is the ratio of the transmitted power to the applied power, is plotted a function of oscillator frequency. The response of the sensor 10 at a room temperature of 25° C. is shown by the solid line that is labeled 80, while the response at 750° C. is shown by the dashed line that is labeled 82. As illustrated in FIG. 10, a seven db loss is noted between the peak of the 750° C. response curve 82 and the peak of the 25° C. response curve 80, with a frequency shift of about 3.5 MHz. Additionally, the inventor observed that additional losses at the higher temperature decreased Q for the sensor from 2123 to 554, thus demonstrating a temperature sensitivity in the response for the device. Similar tests upon a SAW resonator fabricated with Pd transducers operated at a temperature of 250° C. produced only a two db decrease in $|S_{21}|$ over a six week period. Furthermore, the transducer electrodes for both devices showed no metal surface degradation, as verified from an equivalent four probe resistivity measurement and recorded XPS data. The inventor believes that the LGS SAW IDT's fabricated and tested qualify the transducers and devices for harsh environment, high temperature and pressure, modern applications such as combustion engines, high power communications, and gas and oil well applications.

Figure 11:
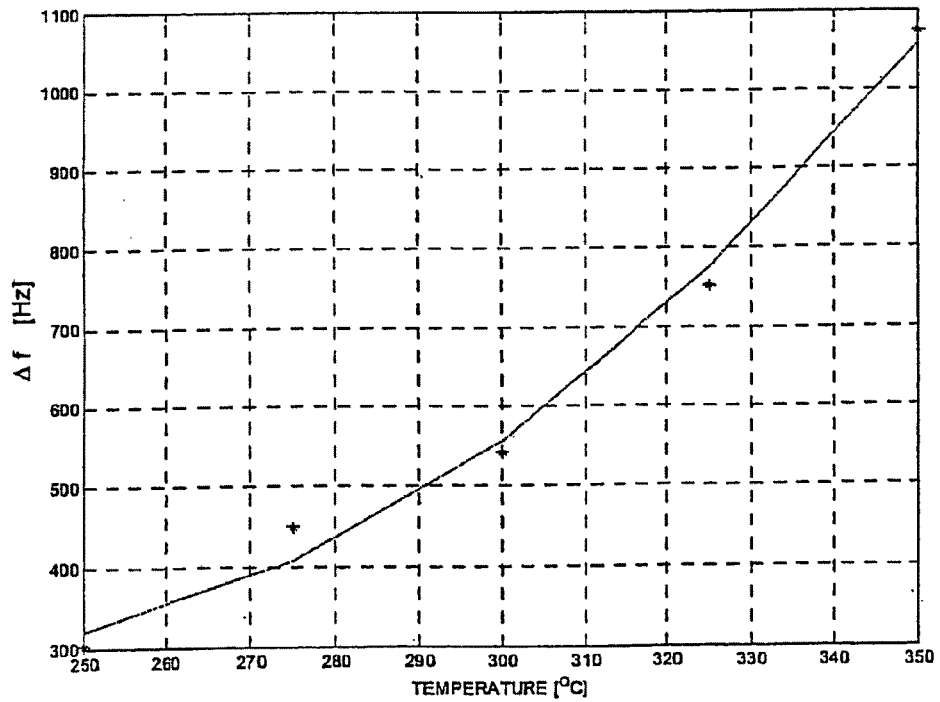
FIG. 11 is an experimentally obtained graph of $\Delta f$ vs. ° C. indicating the removal of oxygen from platinum and the formation of $CO_2$ and $H_2O$.

The inventor also performed gas sensor experiments with a SAW resonator in accordance with the invention having platinum IDT's and reflecting strips deposited upon an adhesive layer of zirconium. The resonator was exposed to $O_2$ for thirty minutes to oxidize the platinum film, followed by exposure to $C_2N_4/N_2$ for 15 minutes. In the temperature range from 250° C. to 350° C., the dominant physical phenomenon observed by the inventor was the removal of surface-bound oxygen from the platinum film of the resonator by the reaction with $C_2H_4$ to form $CO_2$ and $H_2O$. A positive frequency variation, $\Delta f$ from 0.3 KHz at 250° C. to 1.1 KHz at 350° C. was observed and is illustrated by the graph shown in FIG. 11. The positive frequency variations in FIG. 11 consistently indicate removal of mass from the platinum film on the surface of the high temperature LGS SAW sensor. Accordingly, the inventor believes that the sensor 10 may be used to detect the presence of hydrocarbons, CO, $CO_2$, $NO_x$ and $H_2$ in combustion gases.

Figure 8:
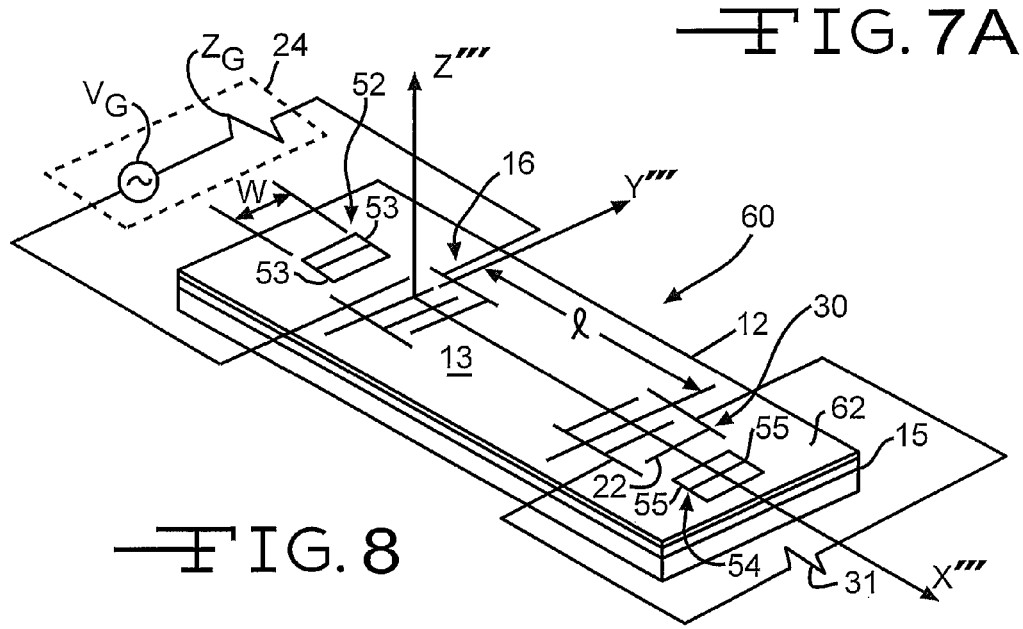
FIG. 8 is a perspective view of an alternate embodiment of the two port Surface Acoustic Wave resonator shown in FIG. 5 that is utilized for the detection of a gas in a high temperature environment.

The inventor also has sputtered a 200 Å thick layer of tungsten trioxide ($WO_3$) over the entire surface of a resonator having platinum IDT's and reflector strips as illustrated in FIG. 8. The resulting device has been successfully used to detect the presence of hydrogen in nitrogen gas by detecting a frequency shift as the tungsten trioxide absorbed hydrogen. The inventor also used a resonator having a 3000 Å thick layer of palladium electron-beam evaporated over a 200 Å thick layer of zirconium to detect hydrogen. The palladium acted as a sponge absorbing up to 900 times its own volume of hydrogen.

In an attempt to increase the sensitivity of the high temperature $WO_3$/Pt LGS sensor to $C_2N_4/N_2$, the inventor exposed the resonator to $O_2$ for thirty minutes, followed by the exposure to $C_2N_4/N_2$ for twenty minutes, in a temperature range from 300° C. to 450° C. Negative frequency variations ($\Delta f$) from 0.8 KHz (at 450° C.) to 1.5 KHz (at 300° C.) were measured between the exposures to $O_2$ and the subsequent exposure to $C_2N_4/N_2$, as shown in the following table:

TABLE 1

Measured frequency variations ($\Delta f$) with exposure to $C_2N_4/N_2$ on a $WO_3$/Pt Resonator

| | Temperature [° C.] | | | |
| --- | --- | --- | --- | --- |
| | 300 | 350 | 400 | 450 |
| $\Delta f$ [KHz] | 1 | 1.5 | 1.2 | 0.8 |

Figure 12:
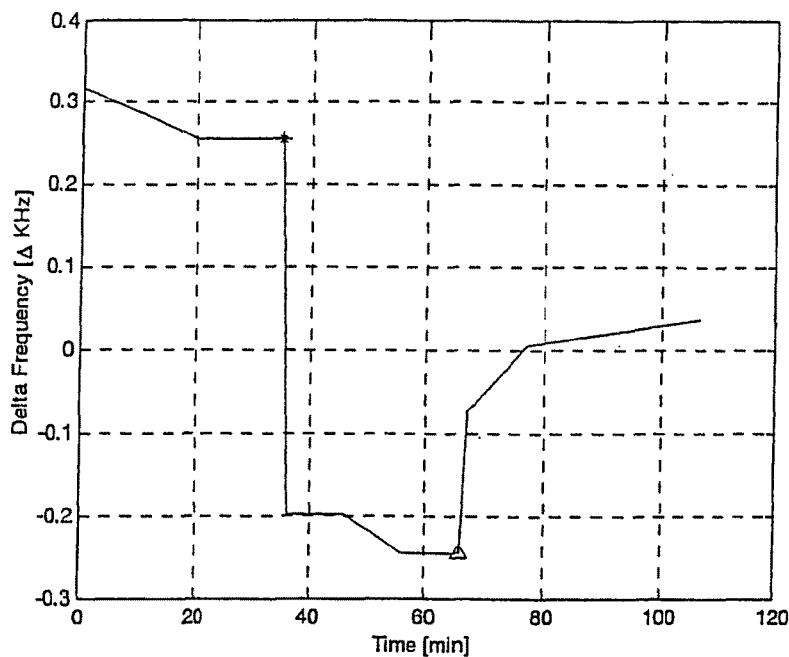
FIG. 12 is a graph of experimental results obtained upon exposure of a Pt transducer delay line with a Pd sensing film deposited in the delay path between the transducers to a mixture of hydrogen and nitrogen gases from an oxygen base line.

The inventor also investigated the sensing of $H_2$ with a Pd film. A two port Pt delay line with a Pd sensing film in the delay path between the IDTs was tested with exposure to $H_2$. The delay line was exposed to $O_2$ for 40 minutes followed by exposure to $H_2$ for 25 minutes, in a temperature range from 250° C. to 400° C. The response of the 200 Å Zr 3000 Å Pd sensing film is illustrated in FIG. 12, where the "*" symbol represents the turning on of the $H_2$ and the turning off of the $O_2$, while the symbol "Δ" represents turning off the $H_2$ and the reintroduction of $O_2$. As can be seen in FIG. 12, there is a 500 Hz frequency shift caused by the exposure to $H_2$ with an $O_2$ baseline at 300° C. The sensing film was also tested at 250° C. with a frequency shift of 200 Hz measured and at 400° C. with a frequency shift of 4 KHz measured.

Figure 13:
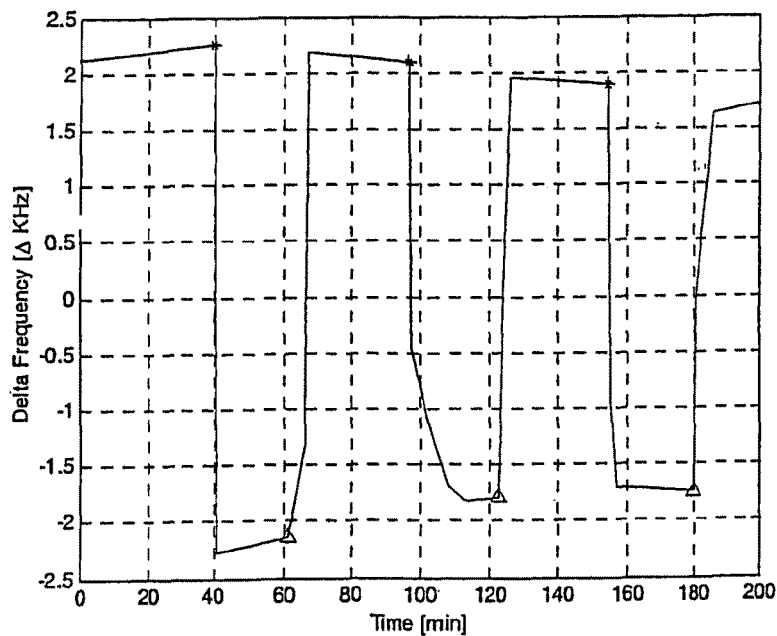
FIG. 13 is a graph of experimental results obtained upon exposure of a two port Pd sensing device without a sensing film to a mixture of hydrogen and nitrogen gases from a nitrogen base line.

The inventor also repeated the above test for a two port Pd resonator without a sensing film at 250° C. with a $N_2$ baseline substituted for the $O_2$ baseline. The results are shown in FIG. 13 where the exposure and recovery are consistent and repeatable with the same magnitude of change of approximately 4 KHz.

The inventor has successfully tested the present invention at temperatures up to 750° C. and believes that the present invention is only limited by the limits of the materials used to fabricate the gas sensors. The inventor further believes that the invention can be used to detect the presence of specific gases at temperatures well in excess of 750° C. In conclusion, the inventor believes that the present invention will be of great commercial interest to the aerospace industry in sensor and frequency control applications, such as fuel leak detection, fire detection, hostile environment detection and frequency control systems.

Further Increase of Operating Temperatures

As described above, for typical surface acoustic wave (SAW) device applications, thin film conductive electrodes are required to pattern the transducer and other structures for generating and manipulating the electromechanical waves in the piezoelectric substrates. For high temperature operation, in particular, a thin film electrode capable of withstanding a harsh environment is required.

Early tests on thin layers of platinum (Pt) electrodes found that the metal aggregated into droplet-like structures, destroying the continuity of the film, a phenomenon referred to as de-wetting. Tests found that this effect can happen at fairly low temperatures (as low as 750° C.) depending on the thickness of the Pt film. The thinner the Pt film, the lower the temperature needed for aggregation. The obvious difficulty arising is that for a SAW device to operate, it is essential that the Pt electrode be on the order of 60 to 100 nm in order to avoid dampening the device's response.

Gold-Platinum Alloy Electrodes

A literature search indicated that Gold-Platinum (Au/Pt) alloys might perform better than either pure gold or platinum films. Various configurations of Au/Pt alloy films were pursued after a review of high temperature film materials and compositions. Samples with compositions 5% Au/95% Pt and 10% Au/90% Pt were investigated. The actual Au content contained in the films was analyzed using X-ray Photoelectron Spectroscopy (XPS) to determine its elemental composition. The integrated intensities of the Pt 4 f and Au 4 f peaks were analyzed to determine the sample composition.

The films were fabricated in a clean-room using an Au/Pt co-deposition technique. The Au/Pt film was co-deposited in an Ultra High Vacuum (UHV) chamber on top of a 10 nm Zr adhesion layer. An e-beam system, which deposited Pt, was operated simultaneously with an effusion cell containing an Au charge. Once both materials had achieved steady evaporation rates, two shutters were lifted in the vacuum chamber and a single layer of 5% Au/95% Pt was deposited to a total thickness of 115 nm. The film thicknesses were achieved by using power settings and deposition rates obtained through system testing prior to the actual deposition. The actual composition of the film was 4% Gold and 96% Platinum, as determined from the XPS measured data. The 10% Au/90% Pt film was deposited upon a Zr adhesion layer using the same process. A XPS analysis of the 10% Au/Pt alloy indicated that the composition was actually 8% Au and 92% Pt.

Each of the Au/Pt films was tested in a Thermolyne high temperature furnace, using a specified ramping profile. The temperature profile was as follows: 350° C. for 2 hours, 550° C. for 5 hours, 750° C. for 8 hours, and 850° C. for 8 hours. Resistance measurement software was used to take data points every minute.

Figure 14:
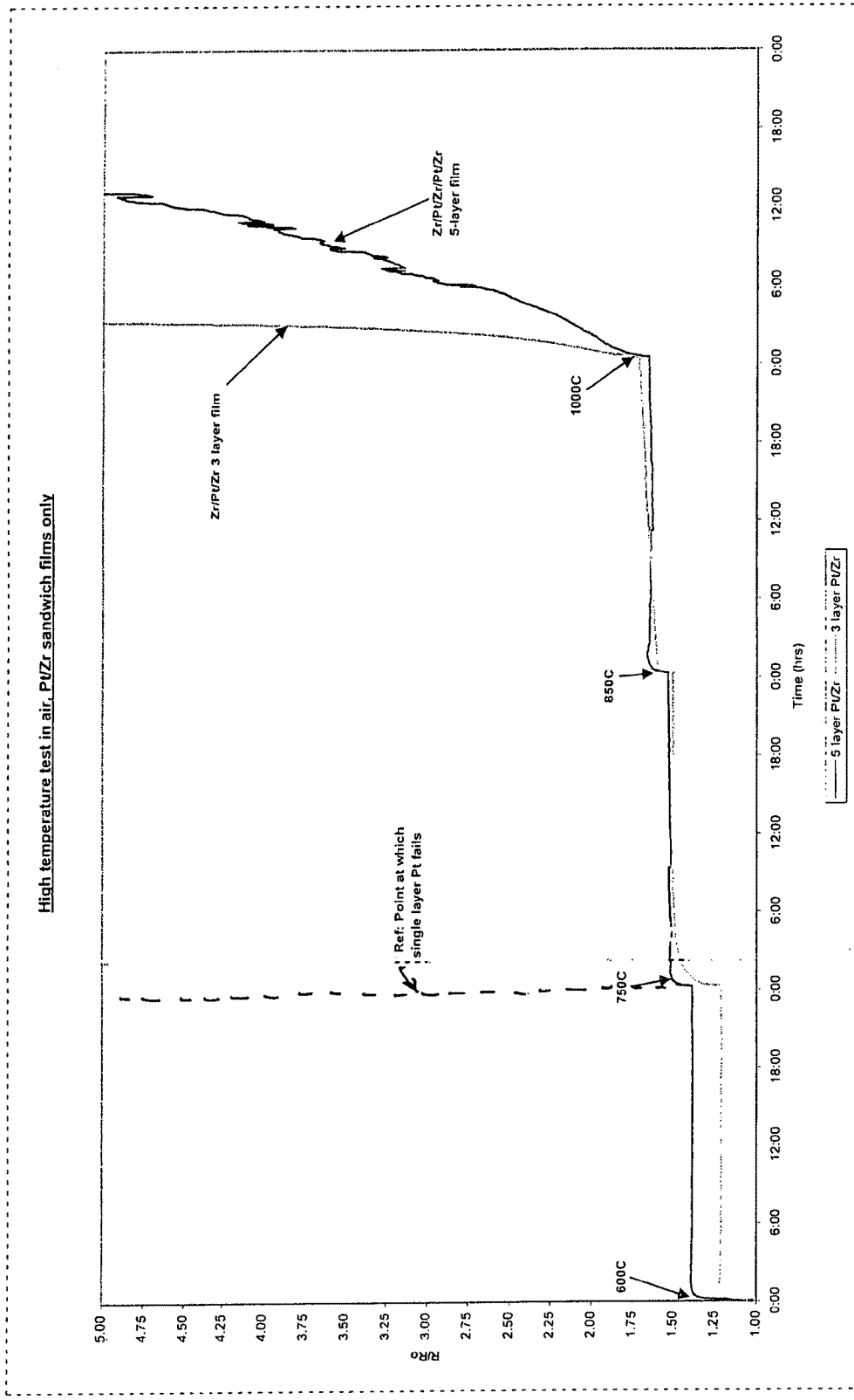
FIG. 14 is a graph of experimental results obtained from high temperature testing of a electrode film in accordance with the present invention that utilizes an alloy for electrodes.

FIG. 14 shows the results of a test containing the two specified Pt/Au alloys of 5%, and 10% Au compositions. The vertical line positioned just beyond the 750° C. temperature mark represents the temperature vicinity at which the pure Pt film fails, as observed from previous experiments. As seen in FIG. 14, the introduction of Au into the Pt prolonged the life of the film, when compared to the single Pt film on top of the adhesion layer. At 5% Au, the film improved from failing quickly at 750° C. to degrading slowly and eventually failing at 850° C. This 5% Au alloy produced a stable resistance at 750° C. as well. When the percentage of Au was increased to 10%, the time to failure at 850° C. also increased. Overall the 10% Au film produced a more stable baseline resistance when compared to the pure platinum film or the 5% Au film. However, both films eventually failed at 850° C., a result less promising than the Pt/Zr sandwich films discussed below. For this reason the inventor did not further pursue Au single layer alloys for use as electrodes.

Layered Platinum Sandwich Films

To further improve performance of the samples, an alternate embodiment of the sensor that utilizes multiple layers of platinum with zirconium and zirconium oxide interlayers for electrodes was adopted. Zirconium (Zr), used for the adhesion of Pt to the piezoelectric substrate, does not migrate into the Pt, and was selected first as a potential material for the layered structure. These sandwich electrode films were deposited using electron beam evaporation techniques on a clean sapphire substrate. The first attempt was to simply place a zirconium cap on the single layer platinum film, as shown generally at 84 in FIG. 15. For identification purposes, this sample was called a three layer film, Zr—Pt—Zr. Note that the zirconium adhesion layer is included in the layer count. The composition was 10 nm of Zr for adhesion, 50 nm of platinum, and a 20 nm Zr cap, however, the invention also may be practiced utilizing other thicknesses for the layers.

A three layer film sample was heated in the Thermolyne model F48015 48000 furnace using a step ramping technique and a resistance and temperature measuring program. In a first test, three layer Zr/Pt/Zr sandwich films were ramped to 600° C. at 1.5°/min and left for 24 hours once the temperature had stabilized. The temperature was then increased to 750° C. at the same ramping rate and left for an additional 24 hours. The sample was ramped to 850° C. and held for another 24 hours and finally increased to 1000° C. until the film failed, as illustrated in FIG. 16.

Figures 15, 17, 18:
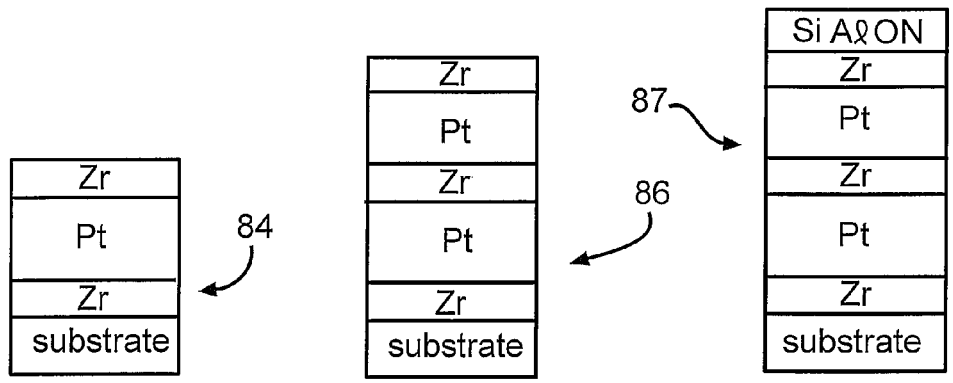
FIG. 15 illustrates the structure of a three layer electrode structure that is in accordance with the present invention.
FIG. 17 illustrates the structure of a five layer electrode film that is in accordance with the present invention.
FIG. 18 illustrates the addition of a protective SiAlON top layer to the five layer electrode film shown in FIG. 17.

A series of platinum/zirconium (Pt/Zr) sandwiches were made with interweaving layers of the two elements. A second electrode film 86 consisted of five layers: a 10 nm Zr adhesion layer, a 30 nm Pt layer, a 10 nm Zr interstitial layer, a second 30 nm Pt layer, and finally a 20 nm Zr cap and is referred to as a five layer film, Zr—Pt—Zr—Pt—Zr, as illustrated in FIG. 17. As with the three layer film, the invention also may be practiced with layer thicknesses that differ from those presented above. For both the three and five layer films, the final layer is a zirconium cap. The 5-layered sandwich produced similar baseline resistance values as the 3-layered Pt film up to 850° C., as also shown in FIG. 16. However, unlike the 3-layered platinum sandwich, the 5-layered sandwich did not produce a baseline drift at 850° C., therefore showing an improvement in the film performance at higher temperatures. The sample lasted a few hours longer at 1000° C. but still went off scale to the Mega-ohm range after 14 hours, as can be inferred from FIG. 16.

For comparison with the previous sandwich film performance, FIG. 16 also shows the performance of a sample fabricated with a 10 nm Zr adhesion layer and 50 nm of platinum on top. No zirconium cap, or overlayer, was added. The single layer result depicted by the dashed line in FIG. 16 shows that the film failed immediately at 750° C. whereas the 3 and 5 layer sandwiches shown in FIG. 16 show that both survived to 850° C. Therefore, both multilayered films showed promise in improving the performance of the single Pt film previously reported. In particular, the 10 nmZr/20 nmPt/10 nmZr/20 nmPt/20 nmZr multilayered sandwich showed slightly superior performance when compared to the 3 layer sandwich, since it increased the time of operation at 1000° C. and produced a baseline without significant drift at 850° C.

SiAlON Passivated Protective Layer

As hypothesized during the early stages of the work, a mechanically protective layer for the SAW device will be necessary, if the device is to be directly exposed to harsh environments. In an early investigation, a 30 nm Silicon Aluminum Oxynitride (SiAlON) film was added to a five Pt/Zr layered sandwich as shown at 87 in FIG. 18 in an attempt to insulate and mitigate the Pt film de-wetting phenomenon. Additionally, the same SiAlON film was deposited on SAW resonators. The films were deposited in an ultrahigh vacuum deposition chamber having a chamber base pressure: $5 \times 10^{-10}$ Torr. The films were grown using reactive magnetron sputtering. Two magnetrons, one with pure silicon and one with pure aluminum, were used. The films were grown to 30 nm at a pressure of 3 mTorr at a temperature of 200° C.

The deposition was carried out with an Argon flow of 12 standard cubic centimeters per minute (sccm), a Nitrogen flow of 10 sccm, and an Oxygen flow of 1.1 sccm. The power supply was radio frequency power (rf) at a level of 110 Watts for Silicon and 130 Watts for Aluminum. The film had a nitrogen-rich composition.

Figure 19:
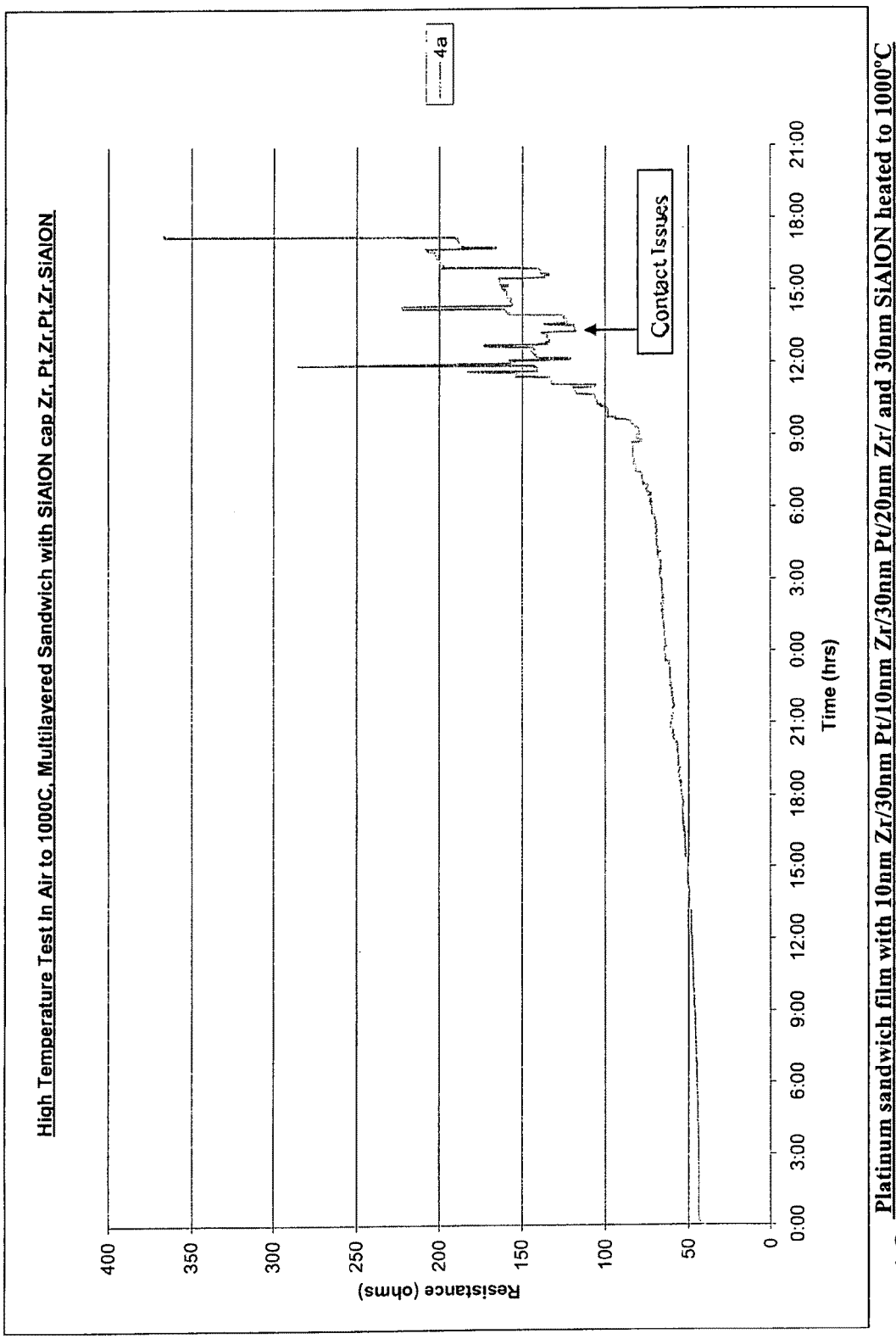
FIG. 19 is a graph of experimental results obtained from high temperature testing of the electrode film shown in FIG. 18.

FIG. 19 shows the resistance response of a 5 layer Pt/Zr sandwich structure with a SiAlON insulating film on the surface. It was ramped straight to 1000° C. and left until failure. Ignoring some contact issues with the connecting wires, the SiAlON coated film lasted over 40 hours at 1000° C.

Figure 20A:
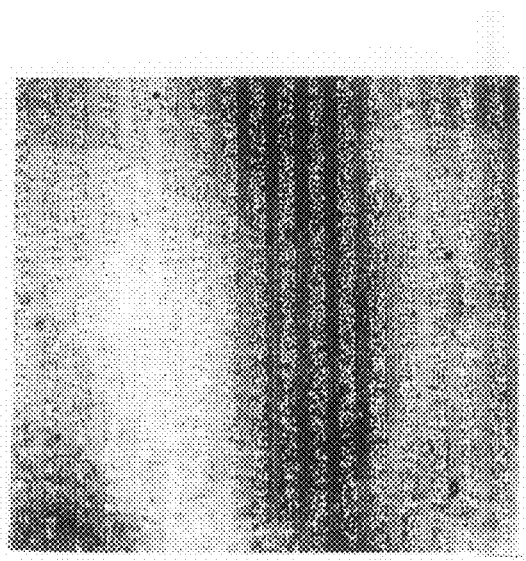
FIG. 20A illustrates the surface of a sensor lacking the protective top layer shown in FIG. 18 after 40 hours of exposure to a high temperature.
Figure 20B:
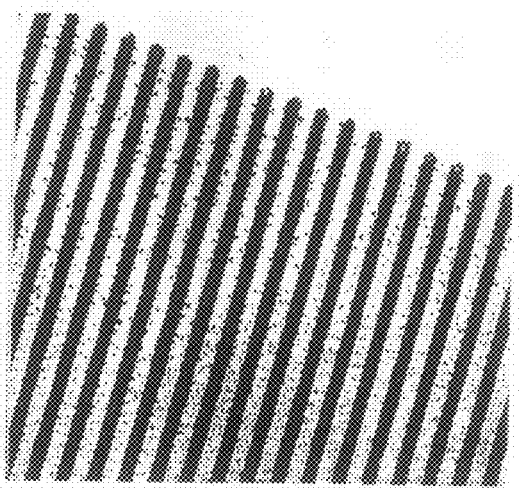
FIG. 20B illustrates the surface of a sensor with the protective top layer shown in FIG. 18 after 40 hours of exposure to a high temperature.
Figure 23:
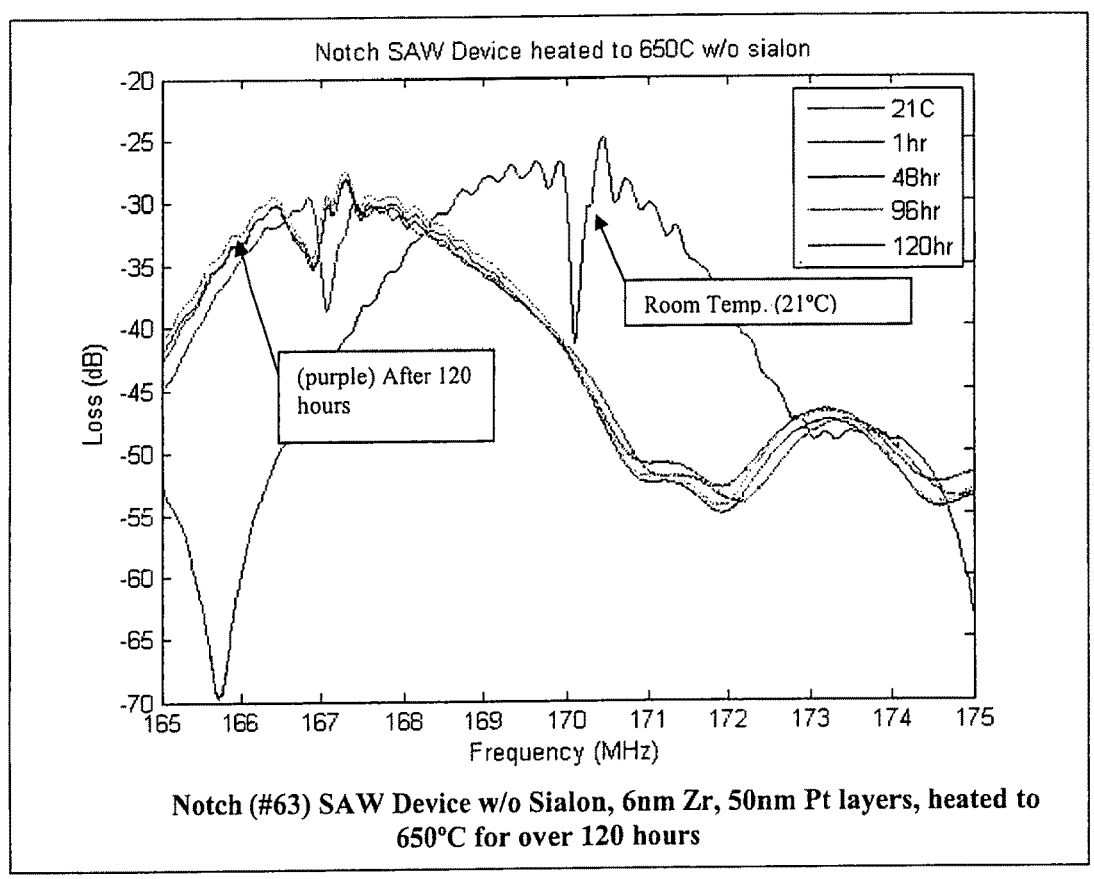
FIG. 23 illustrates the results obtained during high temperature tests of the present invention.
Figure 24:
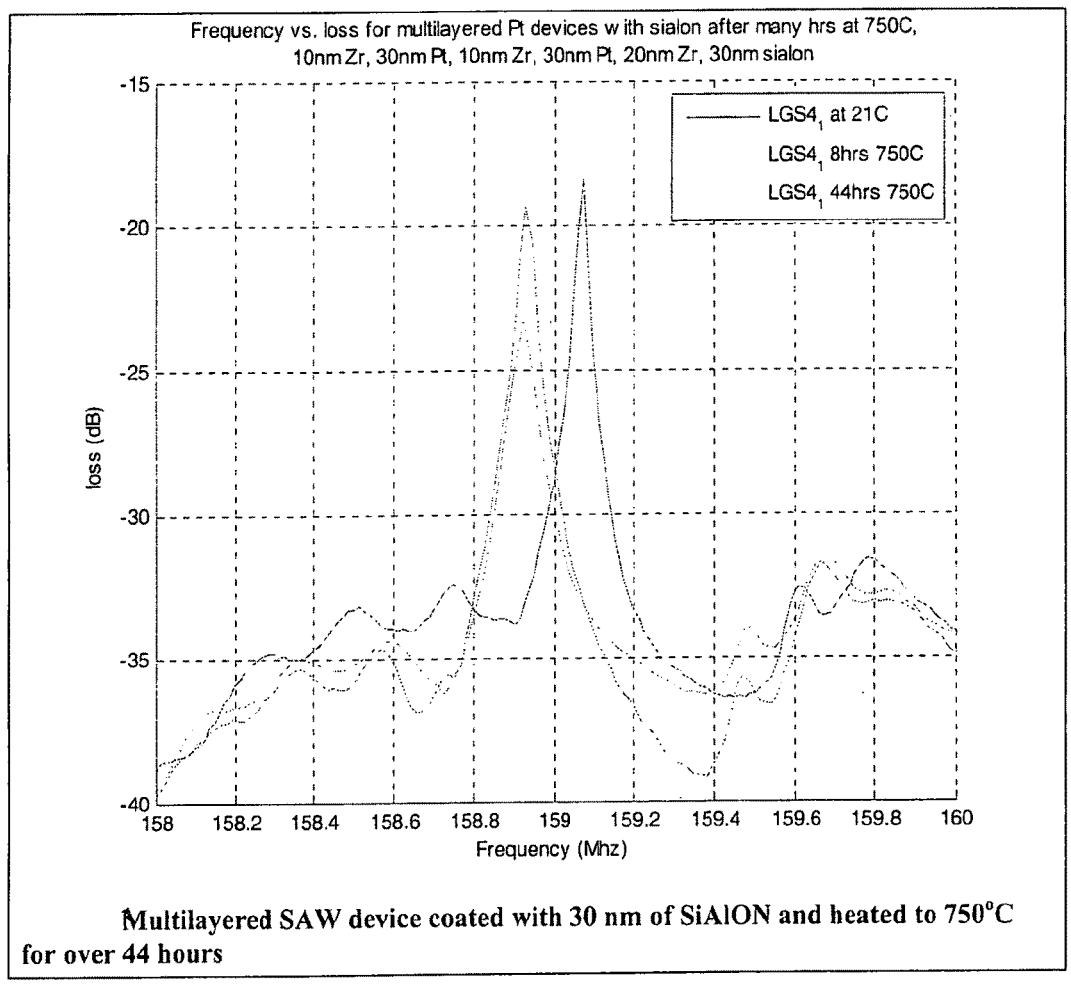
FIG. 24 illustrates frequency responses obtained during high temperature tests of the present invention.

The SiAlON coating provided positive results toward improvement in the high temperature performance of the metallic electrodes deposited on the surface, by retarding film morphology changes, as illustrated in FIGS. 20A and 20B, and therefore increasing the SAW device's high temperature operation limit, in addition to the mechanical protection for the SAW device surface, as shown in FIGS. 23 and 24. It has also been learned from the reported experiments that the SiAlON coating provided temperature compensated operation of the SAW device, since the temperature dependence of the SiAlON coating compensates the temperature behavior of the LGS SAW device. These positive results were carried over to initial experiments with LGS SAW devices at high temperatures. FIG. 20 shows two such LGS SAW devices with 6 nm Zr and 50 nm Pt, heated to 1000° C. with and without an insulating SiAlON top layer. The devices were annealed using a temperature ramping scheme in a Thermolyne model F48015 48000 furnace of 650° C., 750° C., 850° C., and 1000° C. for periods of 24 hours at each intermediate temperature setting, and once the device reached 1000° C., it was left for 40 hours. Both devices were placed in an alumina crucible to prevent particle contamination on the surface of the device from the oven.

FIG. 20A shows a picture of the typical platinum beading or de-wetting experienced in previous high temperature tests. Continuity measurements indicated an open circuit due to the platinum agglomeration. FIG. 20B shows the SAW device with a 30 nm SiAlON top layer. The device still experienced a small amount of agglomeration, but to a much lesser degree. The surface defects did not affect the overall continuity of the device.

All of the surface acoustic wave devices described above were manufactured using photolithographic procedures established in a class 1000 clean room. The resonator devices fabricated have a 4 μm electrode width with a 1:1 mark to space ratio, which yields a center operating frequency of 170 MHz. Multiple devices were fabricated on two different wafers with crystal orientations of Euler angles (0, 0, yr)=(0°, 144°, 24°) and (0, 0, yr)=(0°, 138.5°, 26.2°) respectively. SAW devices with and without a SiAlON overlayer were tested.

Temperature Cycling on Fabricated SAW Devices

An important parallel investigation referred to the capability of the SAW devices to respond repetitively to temperature cycling, under high temperature, harsh environment operation. In the targeted sensor environment, a repetitive device response with temperature cycling corresponds to diminished calibration requirements, and therefore to more reliable sensor operation.

Figure 21:
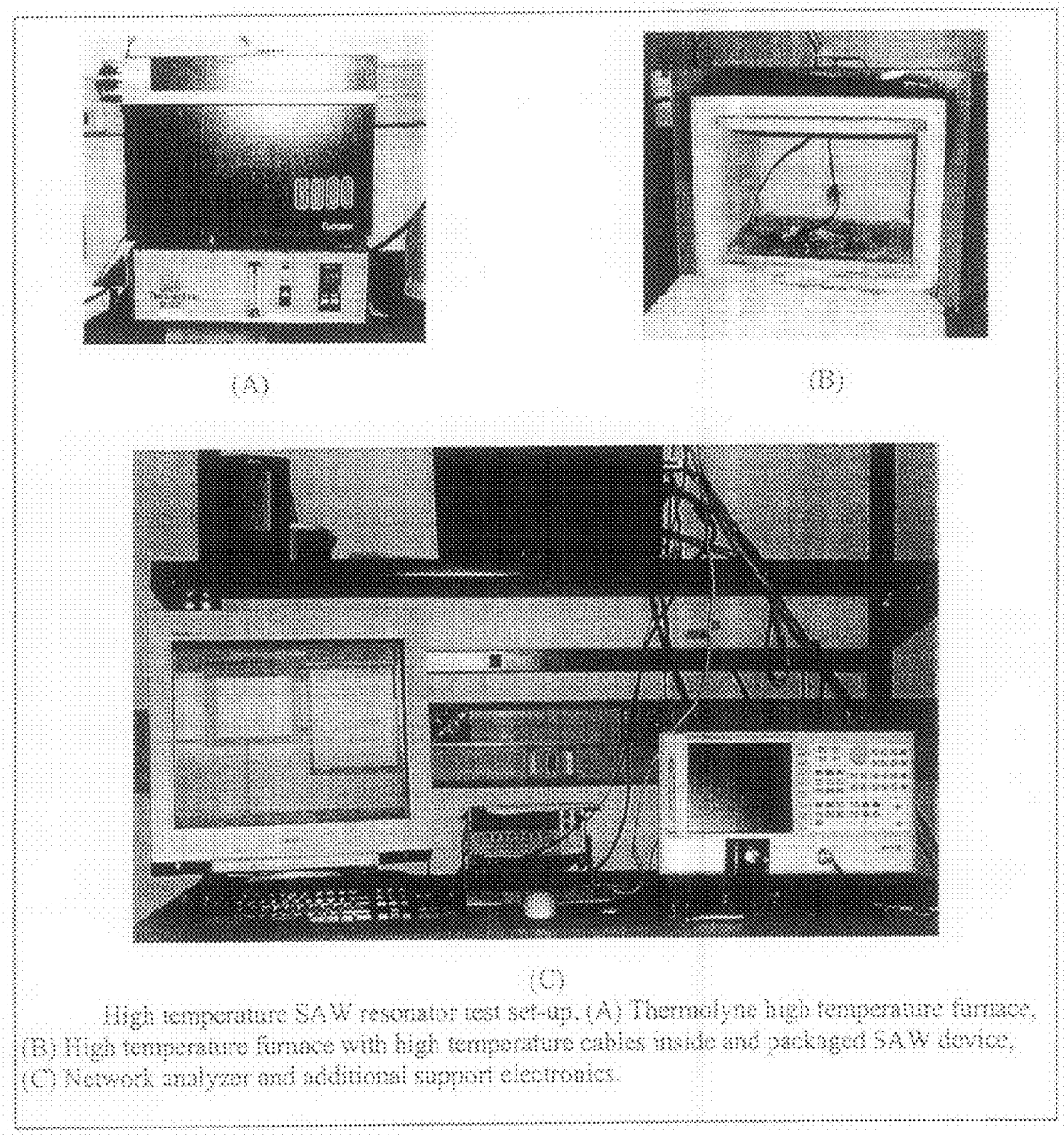
FIG. 21 illustrates a High Temperature Surface Acoustic Wave resonator test set-up used for testing the present invention.

A SAW device was packaged onto an alumina substrate with Pt tracks for a 50 ohm coplanar transmission line which were then attached to multiple high temperature cables. The stainless steel jacketed cables were fed through a hole in the top of the furnace and attached to a network analyzer where each data point was measured. The set-up was calibrated at room temperature at the coaxial connector's end of the high temperature coaxial cables. FIG. 21 shows the components of the high temperature cable test set-up. The temperature settings were changed manually using a controller mounted on the front of the furnace. Each data point was taken once the temperature had stabilized inside the furnace.

Figure 22:
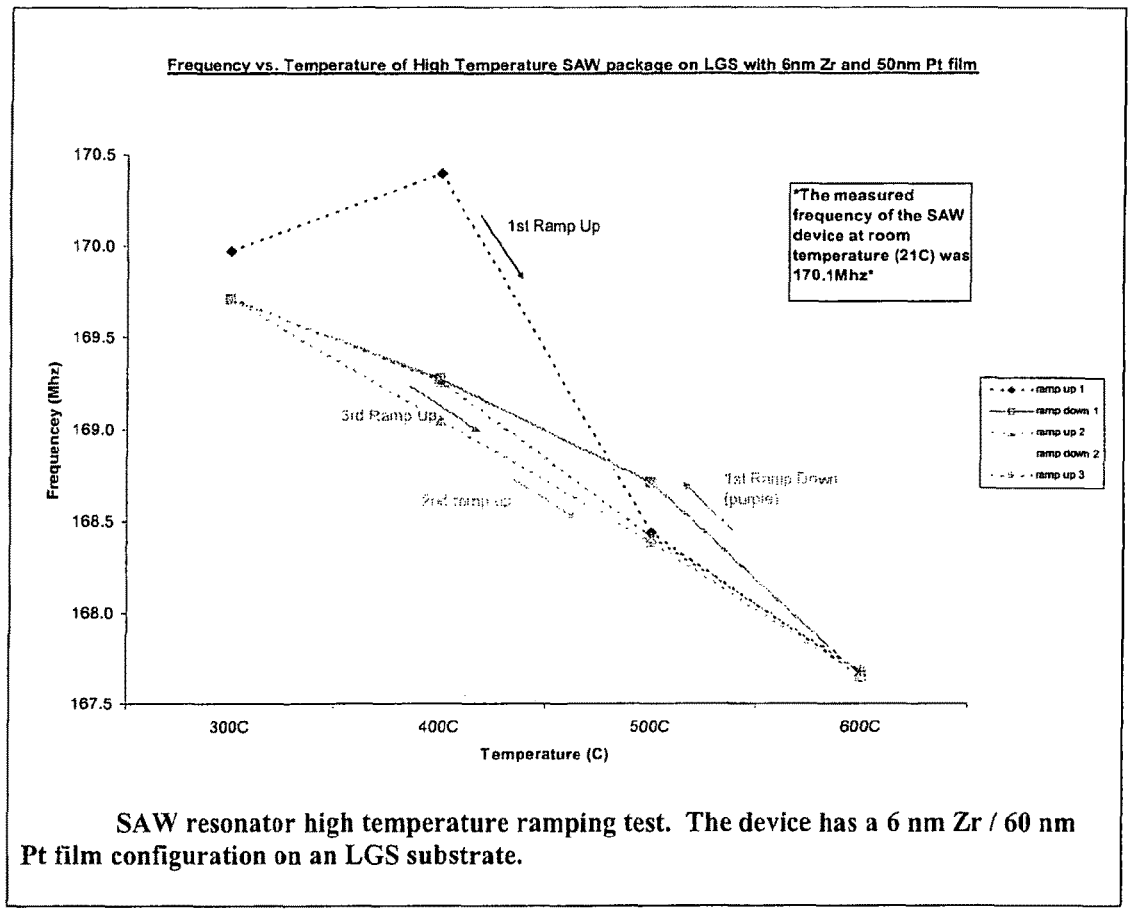
FIG. 22 illustrates the results obtained during high temperature ramping tests of the present invention.

A SAW device with a 6 nm Zr adhesion layer/60 nm Pt top layer configuration was tested for stability response in fluctuating high temperature environments. FIG. 22 shows the SAW frequency vs. temperature results. This single metal layer device was ramped up to 600° C. to avoid reaching temperatures where the single layer film would suffer permanent damage, since the object of this test was to verify the repeatability of the SAW resonator performance. During the first temperature ramp the film became annealed, and the following frequency ramps were more repeatable and stable with temperature. At 400° C. the film appears to go under a phase change, which causes an increase in the resonator frequency. After further increase in the temperature, the frequency decreased. These results show that the Pt based SAW device will simply require a first film annealing after device fabrication for repetitive sensor operation.

The following chart shows the results of data taken at various temperature and time intervals. The Q of the SAW device has been calculated based on the frequency response measurements obtained with the network analyzer. The Q value of the SAW devices dropped as the temperature increased up to 650° C., with the frequency also dropping from 170.1 MHz to 167.2 MHz.

TABLE 2

Test on 6 nm Zr and 50 nm Pt film, #63 SAW device
Frequency measurements with a calculated Q at
multiple temperature intervals

| Baseline measurement at room temperature (21 C.) | | | |
|---|---|---|---|
| Center frequency | 170.1 MHz | | |
| Loss | (41.35) db | | |
| | 3 db loss measurement | | |
| to left of notch | frequency 170.075 MHz | Q = 1170/0.07 | 2430 |
| to right of notch | frequency 170.145 MHz0 | | |

| Baseline measurement after 24 hours at 600 C. | | | |
|---|---|---|---|
| Center frequency | 167.49 MHz | | |
| Loss | (42.07) db | | |
| | 3 db loss measurement | | |
| to left of notch | frequency 167.425 MHz | Q = 167.49/0.137 | 1223 |
| to right of notch | frequency 167.562 MHz | | |

| Baseline measurement after 32 hours at 600 C. | | | |
|---|---|---|---|
| Center frequency | 167.49 MHz | | |
| Loss | (42.09) db | | |
| | 3 db loss measurement | | |
| to left of notch | frequency 167.423 MHz | Q = 167.49/0.13 | 1288 |
| to right of notch | frequency 167.553 MHz | | |

| Baseline measurement after 48 hours at 600 C. | | | |
|---|---|---|---|
| Center frequency | 167.46 MHz | | |
| Loss | (42.02) db | | |
| | 3 db loss measurement | | |
| to left of notch | frequency 167.3967 MHZ | Q = 167.46/0.145 | 1155 |
| to right of notch | frequency 167.532 MHz | | |

| Baseline measurement after 54 hours at 600 C. | | | |
|---|---|---|---|
| Center frequency | 167.46 MHz | | |
| Loss | (40.48) db | | |
| | 3 db loss measurement | | |
| to left of notch | frequency 167.395 MHz | Q = 167.46/0.136 | 1231 |
| to right of notch | frequency 167.531 MHz | | |

| Baseline measurement after 1 hour at 650 C. | | | |
|---|---|---|---|
| Center frequency | 167.20 MHz | | |
| Loss | (33.21) db | | |
| | 3 db loss measurement | | |
| to left of notch | frequency 166.885 MHz | Q = 1167/0.485 | 344.74 |
| to right of notch | frequenncy 167.370 MHz | | |

Long Term High Temperature SAW Device Test With and Without a SiAlON Top Layer

Multiple samples with and without a SiAlON insulation layer were tested in order to observe how the coating would aid film stability at elevated temperatures. The effect of the SiAlON coating on the SAW response was also observed.

Electrical connections were made with 1 mil Pt wire to the SAW device bond pads using a parallel gap welder. Since this is a two-port SAW device, multiple connections for the signal in, signal out and ground were made. There are 6 connections needed for the device to operate properly in our high temperature fixture: one connection on each live bond pad for the signals in and out, and four more for the device ground. There were additional connections made to the device for redundancy. These bonded connections were made prior to the deposition of the SiAlON film due to the bonding uncertainty between SiAlON and platinum.

All of the devices were tested in the Thermolyne high temperature furnace. The temperature was controlled by a Honeywell controller mounted on the front of the furnace. Each temperature was set manually but monitored closely for accuracy and stability for the test. The data points were taken at each time interval but not until the temperature was stable.

A notch resonator having a #63 pattern, 6 nm Zr adhesion, 50 nm Pt, without a Zr cap and without SiAlON on top was fabricated on an LGS substrate with Euler angles (0°, 138.5°, 26.6°). The device was packaged into a high temperature test fixture and tested to temperatures up to 650° C. The resonator has a center frequency of 170 MHz with 4 mm line widths. FIG. 23 shows the results of the notch SAW device over a 120 hour period at 650° C. The increase in temperature shifted the central notch response to a lower frequency and reduced the resonator's Q. The sensor was still operational after 120 hours of exposure to a 650° C. temperature environment. After that, the device response degraded, and further investigation and test repetition is required to identify the cause of the failure, which could be due to the wire bonding, high temperature cables, at the bonding end exposed to high temperature, and packaging.

Two 6 nm Zr/50 nm Pt layered devices and two 10 nm Zr/30 nm Pt/10 nm Zr/30 nm Pt/20 nm Zr layered devices were coated with a 30 nm thick SiAlON layer after attaching the necessary bond leads for electronic measurement. FIG. 24 shows a 5 layer SAW device having a #62 pattern, 10 nm Zr, 30 nm Pt, 10 nm Zr, 30 nm Pt, 20 nm Zr, with 30 nm SiAlON on top which degraded slightly over time. Once the temperature reached 750° C. the loss increased by 3 dB and the frequency shifted from 159.1 Mhz to 158.9 Mhz. After the baseline of the sensor decreased due to the increase in temperature, it stayed at the same frequency. After 44 hours, the frequency was consistent but the loss increased, most likely due to film degradation.

Figure 25:
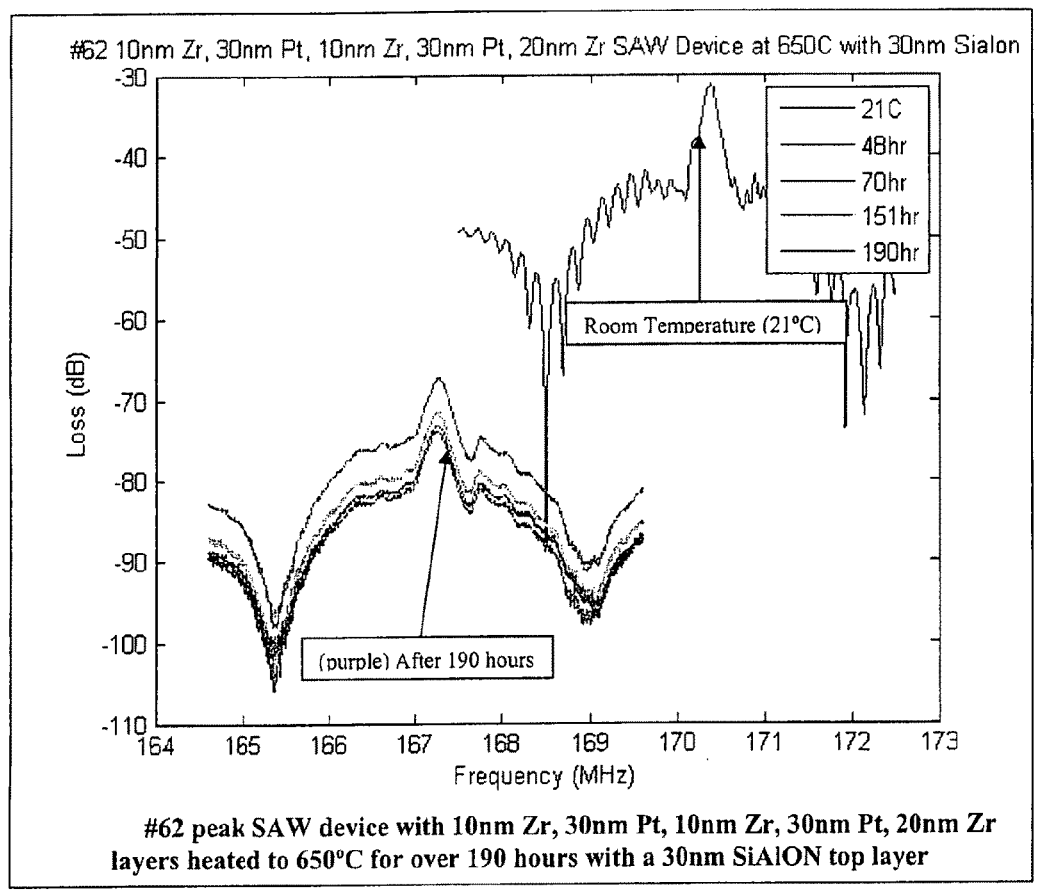
FIG. 25 illustrates additionally frequency responses obtained during high temperature tests of the present invention.
Figure 26:
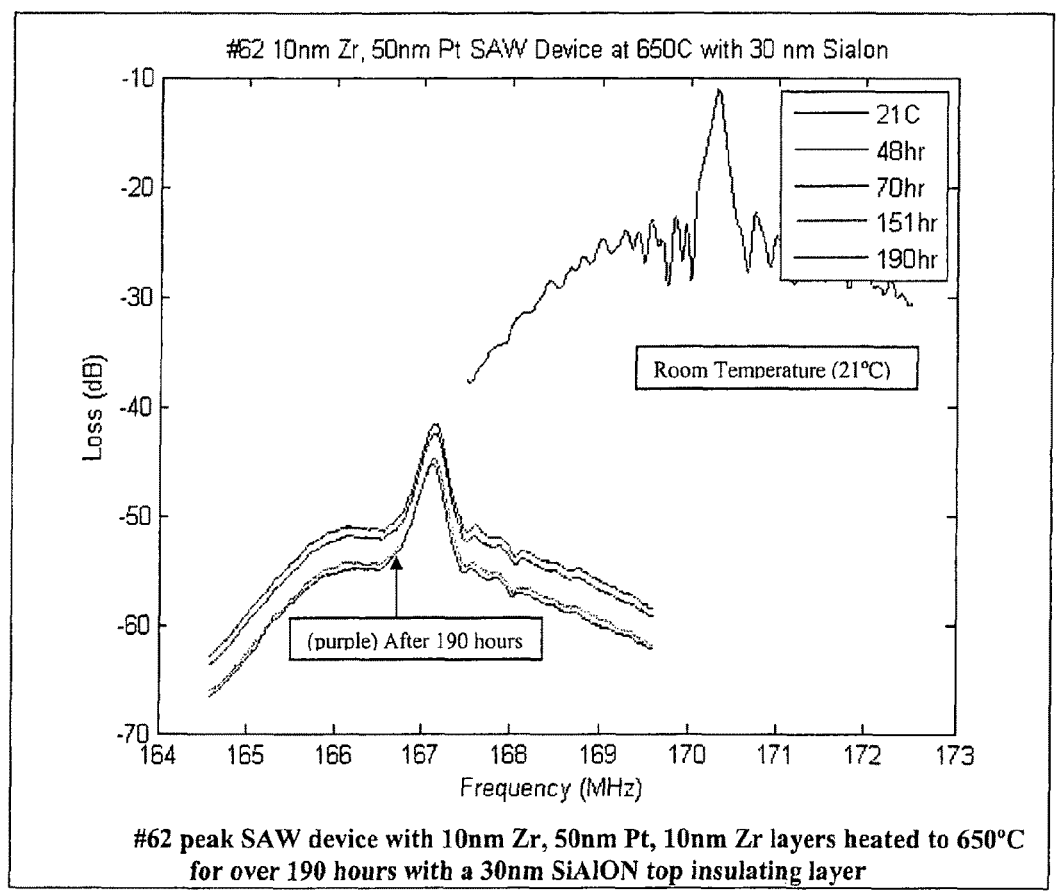
FIG. 26 illustrates further frequency responses obtained during high temperature tests of the present invention.

FIGS. 25 and 26 show the performance of a 5 layer sandwich SAW resonator having a #62 pattern, 10 nm Zr, 30 nm Pt, 10 nm Zr, 30 nm Pt, 20 nm Zr, with 30 nm SiAlON on top, and a 3 layer sandwich SAW resonator having a #62 pattern, 10 nm Zr adhesion, 50 nm Pt, and 20 nm Zr cap, with 30 nm SiAlON on top, respectively. The resonators were tested for 190 hours at 650° C. The devices were still operational after 190 hours. The frequency has shifted and attenuated, but were very stable. After the initial frequency shift to account for the temperature increase it became stable for the remainder of the test. The measured transmission loss increased one or two dB every 40-50 hours depending on the device measured.

For the device structure tested, the 5 layer device whose results are shown in FIG. 25 resulted in a higher transmission loss with respect to both the single layer notch device whose results are shown in FIG. 23 and the 3 layer resonator device whose results are shown in FIG. 26. Regarding the failures of the devices, further experiments are planned to identify the cause(s) after more than two hundred hours of operation, since it could be due to the wire bonding, high temperature cables, at the bonding end exposed to high temperature, and packaging.

From the comparison between FIGS. 24 and 25, it is interesting to notice that the SAW resonator used for these initial investigations showed remarkable difference in terms of the measured insertion loss. In FIG. 24 a room temperature transmission loss of about 18 dB went to 24 dB after about 40 hours of testing at 750° C., whereas in the case of FIG. 25 a much larger 32 dB room temperature transmission loss increased 40 dB when maintained for about 48 hours at a lower temperature of 650° C. These results show that further experiments, analysis, and design are required to determine how much of this observed transmission loss is due to film fabrication, film performance, device design, bonding performance, device packaging, and crystal orientation response at different temperatures.

Additional Multi-Layered Electrode Films

Figures 27, 28:
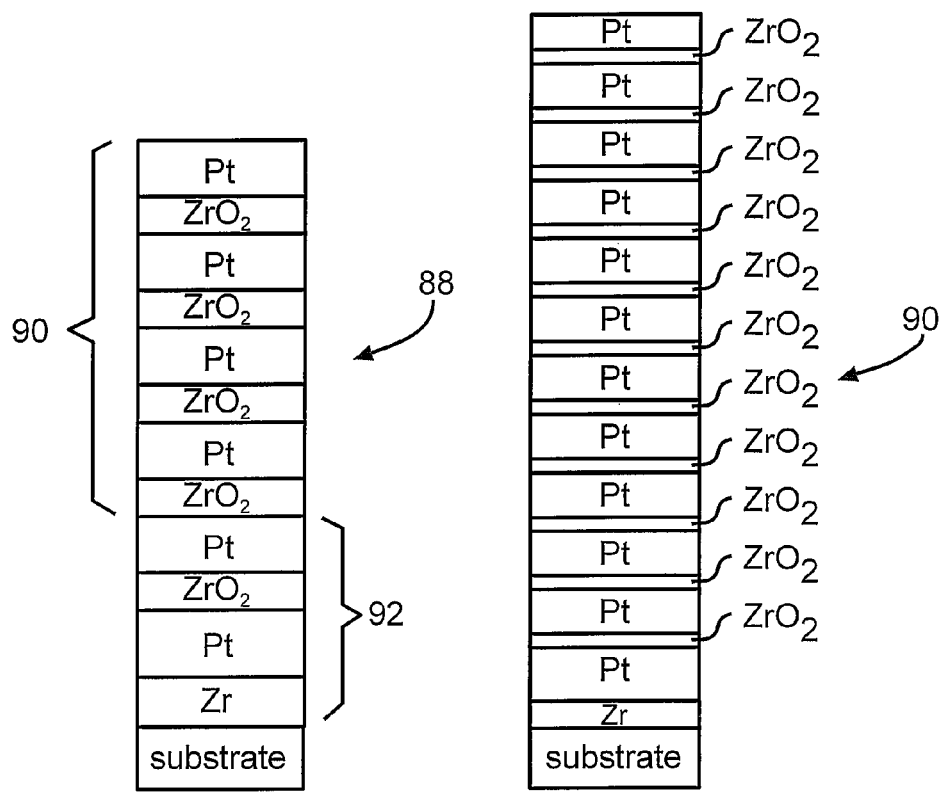
FIG. 27 illustrates the structure of a twelve layer electrode film that is in accordance with the present invention.
FIG. 28 illustrates the structure of a twenty four layer electrode film that is in accordance with the present invention.

Due to the relative success of the three and five layer film sensors, twelve and twenty four layer structures 88 and 90, as shown in FIGS. 27 and 28, respectively, were investigated. Two additional changes were made in the layered structures; first, no zirconium cap was used, and second, the intermediate zirconium layers were replaced with zirconium oxide, as illustrated in FIGS. 27 and 28. The $ZrO_2$ layers were formed by depositing Zr in the presence of molecular oxygen admitted to the chamber at a flow of 0.2 standard cubic centimeters per minute. When depositing the initial zirconium adhesion layer, oxygen was not introduced into the chamber. Hence, the adhesion layer is pure zirconium. As shown in FIG. 27, the twelve layer sensor 88 is divided into two sets of layers, one set 92 with 5 angstrom $ZrO_2$ intermediate layers, which are referred to as a 5 angstrom films, a second set 94 with a 15 angstrom $ZrO_2$ intermediate layer, which is referred to as a 15 angstrom film. The twenty four layer sensor 90 uses a 15 angstrom $ZrO_2$ intermediate layer throughout. In each case, the total thickness is between 1000 and 1200 angstrom unless otherwise noted. It will also be appreciated that the invention also may be practiced with other layer thicknesses than those listed above.

The 12 layer sensor 88 was fabricated using an electron beam deposition system located inside a clean room. The sensors were packaged using bonding equipment and monitored throughout each test with resistance measurement equipment.

FIG. 29 shows a comparison of 12 layer films having either a 5 angstrom film or a 15 angstrom film. Note that both films show a relatively flat baseline at 850° C. At 950° C., the resistance of the 5 angstrom film goes off scale whereas the resistance of the 15 angstrom film increases gradually, by 22 ohms over a four hour time span. On heating to 1000° C. the resistance of the 15 Angstrom film increases rapidly, indicating agglomeration and loss of continuity at that temperature. Both films showed remarkable improvement over the single layer platinum film. Inspection with an optical microscope of the multilayer films following heating showed the same type of agglomeration observed after heating single layer films. The twelve layer films show considerable improvement over the single layer platinum film as well as the single layer Pt—Au alloy films, neither of which survived to 950° C.

Selected multiple layer films were placed in an ultra-high vacuum (UHV) system and annealed to 1000° C. for two hours as described earlier since it had been determined that vacuum annealing had improved the performance of previous single layer films. The effect of the pre-annealing treatment on the 5 and 15 angstrom 12-layer films is shown in FIG. 30. The pre-anneal significantly improved the performance of the 5 angstrom film. Instead of losing continuity at 950° C., the film survived to 1000° C. with a relatively flat baseline at 950° C. However, the pre-anneal significantly degraded the performance of the 15 angstrom film, a repeatable result. Therefore, the better films were a Pt/5 angstrom $ZrO_2$ pre-annealed sample and Pt/15 angstrom $ZrO_2$ sample without the pre-anneal.

Twelve layer Pt-10% Au samples with 15 angstrom Zirconium Oxide interlayers (not shown), similar to the above 12 layer Pt/$ZrO_2$ samples, were also fabricated. After fabrication and dicing, one platinum-gold alloy film was pre-annealed in vacuum as described above. The two alloy samples were then tested against a single layer platinum film. These results are shown in FIG. 8 with data for the 12-layer 15 angstrom Pt/$ZrO_2$ sample for comparison.

Using the gold-platinum alloy in this multi-layer configuration provided some improvement compared to the single layer gold-platinum alloy results. However the film did not perform quite as well as the 15 angstrom 12-layer Pt/$ZrO_2$ sample. The gold alloy film resistance increased by approximately 68 ohms in four hours at 950° C. while the sample with only platinum and $ZrO_2$ increased by only 21 ohms in the same four hour time span. Due to the inability of the gold alloy film to withstand elevated temperatures better than pure platinum films, the gold alloys were not pursued further at the present time.

Additionally, multi-layer films using a platinum-rhodium (Pt—Rh) alloy (not shown) were fabricated and tested. The Pt-10% Rh films were fabricated using the electron beam deposition system in a clean room using Pt-10% Rh alloy as a starting material. Deposition rates and settings for the alloy were based on settings used for pure Platinum depositions. FIG. 32 shows a comparison of test results obtained with a 12 layer 15 angstrom Pt-10% Rh/$ZrO_2$ film and a similar 15 angstrom twelve layer Pt/ZrO$_2$ film with pure Platinum layers. The Pt—Rh film had more stable resistance values at high temperatures than the Pt film. The Pt—Rh film resistance was stable at 850° C. and 950° C. while at 950° C. the twelve layer Pt/ZrO$_2$ film degraded slightly over time. Once the temperature was increased to 1000° C. the twelve layer Pt/ZrO$_2$ film degraded quickly until total failure while the Pt-10% Rh film lasted the full sixteen hours without going off scale. Its baseline resistance increased by 178 ohms over a 16 hour period at 1000° C. Once the furnace was turned off and the film was allowed to cool to room temperature, it recovered to approximately 100 ohms resistance from just under 300 ohms at its maximum. It is interesting to note that once the temperature was increased to 950° C. the Pt—Rh alloy film experienced a significant resistance decrease. The inventors believe that this may be due to a film annealing/recrystalization phenomenon of the Pt—Rh alloy material. This film combination improved significantly in performance over both the Pt/ZrO$_2$ film and the single layer Platinum film.

FIG. 33 shows the overall comparison of the best twelve layer films of each type along with results from a single layer platinum film. The untreated twelve layer Pt-10% Rh film clearly has the best high temperature performance among this group of films. Although it does show increasing resistance at 1000° C., it did not fail. FIG. 34 shows the recovery of the Pt-10% Rh film after sixteen hours at 1000° C.

In order to further improve high temperature stability, samples with more zirconia interlayers and thinner Pt or Pt-alloy layers (not shown) were fabricated to determine whether the additional zirconia layers and the resulting thinner Pt or alloy layers would further retard morphological changes in the films. Accordingly, the twenty four layer films were deposited in an ultra high vacuum chamber configured to allow simultaneous electron beam deposition of two different materials. In the case of layered materials, this allowed growth of the two types of layers to be easily alternated by opening and closing shutters to the appropriate evaporation source.

Although the reported percentage of Rh in the Pt alloy used was 10%, the inventors envision that using different Rh contents in the Pt/Rh alloy might improve the high temperature performance. Accordingly, the inventors contemplate practicing the invention with a Pt alloy containing a percentage by weight of Rh within the range or two to 60 percent.

The invention also contemplates replacing Rh in the Pt alloy with Iridium (Ir) for high temperature applications. Again, the inventors contemplate practicing the invention with a Pt alloy containing a percentage by weight of Ir within the range or two to 60 percent.

In addition, the invention further contemplates using pure Rhodium or pure Iridium films as alternatives for Surface Acoustic Wave device electrode film.

The first film fabricated was a Pt/ZrO$_2$ film consisting of twelve 90 Angstrom thick layers platinum interleaved with eleven 15 Angstrom thick layers of ZrO$_2$. All samples began with a 100 Angstrom zirconium adhesion layer. For the first film fabricated, the total thickness was thinner than anticipated, approximately 800 angstroms. After dicing, one sample was pre-annealed in vacuum. Results are shown in FIG. 35 with a comparison to a single layer Platinum film. Pre-annealing this film did not improve its performance at elevated temperatures. However the Platinum 24 layer film did outperform the 12 layer Platinum sample at 1000° C. and did not go off scale. These results for the thinner-than-usual film were encouraging and were similar to the results obtained with the 12 layer Pt—Rh film. Since the Pt—Rh multi-layer films outperformed pure Platinum multi-layer films, a 24 layer Pt-10% Rh film was produced in the UHV chamber.

FIG. 36 is a comparison of 12 and 24 layer samples. Somewhat surprisingly, only a small difference is seen between the 12 layer Pt-10% Rh film and the 24 layer Pt—Rh film. Also somewhat unexpectedly, the 24 layer Pt-10% Rh film showed little or no significant improvement compared to the 24 layer Pt film. Three films, the 12 layer Pt-10% Rh /15 Angstrom ZrO$_2$ film, the 24 layer Pt/15 angstrom ZrO$_2$ film, and the 24 layer Pt-10% Rh/15 angstrom ZrO$_2$ film, showed a stable baseline for 4 hours at 950° C. These films showed a slow rise at 1000° C. which did reach the M-ohm scale during the 16 hour test.

As a comparison, FIG. 37 shows a comparison of various multi-layered films using the same constituent materials and the same ZrO$_2$ interlayers. For the case of pure platinum films, adding layers and reducing the Pt layer thicknesses continually improves the performance at least up to the case of 24 layers. However, in the case of the Pt—Rh alloy, which outperforms pure platinum films for 12 or less layers, there is unfortunately little additional improvement on going to 24 layers.

Platinum Alloy Co-Deposited with Zirconia Films

A single layered film consisting of a homogeneous Pt—Rh—ZrO$_2$ composition was fabricated. The film was developed by means of a co-deposition technique being performed in an UHV chamber using electron beam deposition technology. The three materials were deposited simultaneously in an oxygen rich environment and monitored by on board electronics for rate verification. A 100 angstrom zirconium adhesion layer was deposited prior to the co-deposited top layer film. The concentration of Pt—Rh to ZrO, is 8 to 1 or 12.5% ZrO$_2$. This ratio is based on material weight. The total thickness of the film is between 1000 to 1100 angstroms. This type of film was pursued in order to investigate how a fine dispersion of zirconia into the metallized film affects its ability to resist the typical agglomeration phenomena experienced at elevated temperatures. The first step was to deposit the film in a single layer (Zr/Pt—Rh—ZrO$_2$) scenario. The film was then tested in a temperature ramp previously used and is as follows: 350° C.-1 hr, 550° C.-2 hrs, 750° C.-2 hrs, 850° C.-4 hrs, 950° C.-4 hrs, 1000° C.-16 hrs. New strips of the film were used in each test. No film was used in consecutive tests. Next the co-deposited single layer film was tested long-term at set temperatures of 800° C., 850° C., 900° C., and 950° C. for periods exceeding 150 hrs while taking resistance measurements of the film every 2 minutes using in-house software and support electronics. FIGS. 38 and 39 show the improved performance of this film with respect to the other films originally investigated so far.

High Temperature SAW Device Tests with Co-Deposited Layer

The single layer co-deposited film was used to fabricate an LGS resonator at 170 Mhz center frequency (at room temperature, 21° C.). The film was approximately 1150 angstrom total thickness with a 12.5% ZrO$_2$ content. It was packaged into a high temperature set-up that was fabricated in-house and then attached to the necessary support electronics that enables us to take periodic frequency and loss measurements through a network analyzer. This requires the use of a high temperature coaxial cable specially designed to be able to withstand temperatures up to 850° C.

The device was step ramped to 350° C. and held there for 17 hrs, 550° C. for 24 hrs, 750° C. for 25 hrs, 800° C. indefinitely for this long term test. The device was left at each temperature for longer periods of time in order to allow the film to anneal itself and produce a stable baseline at each temperature before it is stepped to a higher setting. As seen from FIG. 40, the annealed film and the device response are operating and stable for over 358 hours of testing. The frequency response remained stable over the 358 hours of testing performed so far.

Machining of "Flip-Chip" and Bonded Package Materials

The base plates on the high temperature set-ups for "flip-chip" and bonded packages must have the ability to withstand high temperature environments without deteriorating. Currently the base plates are made of titanium but other potential replacements are being pursued. The inventors have done searches for high temperature alloys that might fit their application. The targeted alloys had to be durable and easy to machine in order for use as replacements for the titanium base mounting plates in the high temperature test fixture currently being used.

High temperature molybdenum and tantalum nuts and screws have been tested in a bonded package. The pieces were heated in a Thermolyne model F48015 48000 furnace to 650° C. for over 120 hrs. Once removed they had oxidized to the point that there was nothing left of the metal. When attempting to remove the nuts and bolts they turned into a powder-like substance and broke off whenever pressure was applied with ease. Both materials proved to be inappropriate for the desired high temperature packing.

Three other high temperature alloys have been tested. Two samples of nickel alloys were obtained from McMaster-Carr. The first was Alloy HX, also known as Inconel HX or Hastelloy HX. The second was Alloy C276, also known as Inconel C276 and Hastelloy C276. Also obtained were six Inconel 600 screws and nuts size #4-40.

One coupon of Hastalloy HX and Alloy C276, along with an Inconel 600 screw and nut, were placed in a ceramic crucible with a cover and placed in a furnace. The alumina crucible was used to prevent any debris or contaminants from the furnace depositing on the surface of the alloys. The furnace was set to 800° C. and left on for two hours, then manually turned off and allowed to cool to room temperature. During the test, alloy HX turned a bluish color, while Alloy C276 had a more orange/reddish appearance. The Inconel 600 screw and nut had a shiny luster before heating and after were a charcoal grey. Mechanically the nuts and bolts had shrunk due to the elevated temperatures but were still able to be used. The threaded holes on the coupon were still intact as well.

In another test, one Inconel 600 nut and screw as well as two nickel based alloys: Hastalloy HX and C276 were placed in an alumina crucible. The crucible was placed inside the furnace, which was then set to 1000° C. After 3 hours, the furnace was to be shut off manually using the controller on the front panel. However, because of a controller malfunction it is believed the furnace ran on a 100% duty cycle for three hours, until it was turned off manually. Approximately 15 minutes after shut-down, the controller was reset and showed a furnace temperature of 1136° C. (the controller did not output a temperature during its malfunctioning state.) It is believed that the furnace reached over 1200° C. during this test. During the test, both samples and the fasteners turned a charcoal grey color. The screw lost material on its threads, although it is difficult to determine if the nut lost material as well. The Hastalloy HX sample looked slightly better than the C276 sample as the C276 has a rough pitted surface, while 1-1X has a smoother surface.

For a third test, a new sample of Alloy HX was cut and weighed before heating to 1000° C. as well as one Inconel 600 nut and screw. All of the samples were then put into an alumina dish, and placed in the furnace. Using the manual programming feature on the oven controller, the temperature was ramped to 1000° C. and left for 3 hours. After 3 hours the furnace was shut off and the samples were then allowed to cool to room temperature. Once at room temperature all of the pieces were weighed again. The results are shown below in Table 3

TABLE 3

| Mass Gain of selected alloys after 3 hours at 1000 C. | | | |
|---|---|---|---|
| | Alloy HX | Inconel 600 | |
| | Sample | Screw | Nut |
| Pre-Bake Mass | 16.6369 | 0.5590 | 0.5358 |
| Post-Bake Mass | 16.6397 | 0.5596 | 0.5362 |
| Mass Difference | 0.0028 | 0.0006 | 0.0004 |
| % Difference | 0.0168% | 0.1073% | 0.0747% |

Table 3 shows that all of the mass increase in the samples is due to oxidation products. The overall largest percentage difference taken before and after heating turned out to be the inconel 600 screw with a 0.1073% difference. The hastalloy HX did oxidize but still appears to be in better physical condition then the C276 alloy. The inconel nuts and screws held up to the 1000° C. temperatures and after heating, the screws threads were tested in the threaded hole tapped in each sample. There were no problems with the screw or sample threads. Another sample of the hastalloy was tested with the screw threaded into the tapped hole. The sample was ramped to 1000° C. in order to see if the screw would seize under the elevated temperatures. There was no thread seizure experienced with the inconel nuts and screws after heating to 1000° C.

The principle and mode of operation of this invention have been explained and illustrated for both a single conductive layer film and 3, 5, 12 and 24 layer films, it must be understood that this invention may be practiced otherwise than as specifically explained and illustrated without departing from its spirit or scope. Thus, the invention contemplates using any number of multiple layers within the electrode films. Also, it will be appreciated that the invention also may be practiced with Shear Horizontal SAW, Pseudo SAW and High Velocity Pseudo SAW modes of wave propagation. Additionally, while the invention has been illustrated and described in terms of a Surface Acoustic Wave Device, it will be appreciated that the thin film electrodes also may be utilized in a wide range of other high temperature applications requiring ultra-thin film conductive electrodes. Such high temperature applications include semiconductor based devices, such as, for example, Field Effect Transistors (FET's), bipolar transistors, diodes, Application Specific Integrated Circuits (ASIC's) and resistive sensors (not shown).

What is claimed is:

1. An ultra-thin electrode comprising:
   a substrate;
   an adhesive layer formed from a material that includes zirconium deposited upon said substrate; and
   an electrically conductive layer deposited upon said adhesive layer that is formed from a material having an excellent thermal stability and a high melting temperature, said electrically conductive layer including at least two layers formed from an electrically conductive material having an excellent thermal stability and a high melting temperature with each two of said layers of electrically conductive material having an interstitial layer that includes zirconium disposed therebetween.

2. The electrode according to claim 1 wherein at least one of said interstitial layers includes Zirconium Dioxide ($ZrO_2$).

3. The electrode according to claim 1 further including a protective layer deposited over said electrically conductive layer.

4. The electrode according to claim 3 wherein said protective layer includes Silicon Aluminum Oxynitride (SiAlON).

5. The electrode according to claim 4 wherein said electrically conductive material is one of the group of platinum, palladium, an alloy of platinum, an alloy of palladium, rhodium and iridium.

6. The electrode according to claim 5 wherein said alloy of platinum includes one of the group of gold, rhodium and iridium.

7. The electrode according to claim 5 wherein the electrode includes annealed components that were annealed at approximately 1000° C. for at least two hours in an ultra-high vacuum annealing system.

8. The electrode according to claim 4 wherein said electrically conductive material is a composite layer of platinum-rhodium and zirconium formed by depositing a platinum-rhodium alloy simultaneously with zirconium upon said adhesive layer in an atmosphere containing oxygen.

9. The electrode according to claim 7 wherein the electrode is included in a Surface Acoustic Wave (SAW) device and further wherein said substrate is formed from a material selected from the group of the LGX family of crystals and gallium phosphate crystals, the substrate having a SAW propagation surface upon which said adhesive and electrically conductive layers are deposited.

10. The electrode according to claim 7 wherein the electrode is included in a semiconductor device.

11. The electrode according to claim 1 wherein said adhesive layer is a first layer formed from a material that includes zirconium and further wherein the electrode includes a second layer that includes zirconium that is deposited over said electrically conductive layer.

12. The electrode according to claim 11 wherein said electrically conductive material is one of the group of platinum, palladium, an alloy of platinum, an alloy of palladium, rhodium and iridium.

13. The electrode according to claim 12 wherein said alloy of platinum includes one of the group of gold, rhodium and iridium.

14. The electrode according to claim 12 wherein the electrode includes annealed components that were annealed at approximately 1000° C. for at least two hours in an ultra-high vacuum annealing system.

15. The electrode according to claim 11 wherein said electrically conductive material is a composite layer of platinum-rhodium and zirconium formed by depositing a platinum-rhodium alloy simultaneously with zirconium upon said adhesive layer in an atmosphere containing oxygen.

16. The electrode according to claim 14 wherein the electrode is included in a Surface Acoustic Wave (SAW) device and further wherein said substrate is formed from a material selected from the group of the LGX family of crystals and gallium phosphate crystals, the substrate having a SAW propagation surface upon which said adhesive and electrically conductive layers are deposited.

17. The electrode according to claim 14 wherein the electrode is included in a semiconductor device.

18. An ultra-thin electrode comprising:
a substrate;
an adhesive layer formed from a material that includes zirconium deposited upon said substrate; and
an electrically conductive layer deposited upon said adhesive layer that is formed from a material having an excellent thermal stability and a high melting temperature, said electrically conductive layer being a single layer of material selected from the group of platinum, palladium, an alloy of platinum, an alloy of palladium, rhodium and iridium.

19. The electrode according to claim 18 wherein said alloy of platinum includes one of the group of gold, rhodium and iridium.

20. The electrode according to claim 18 wherein the electrode includes annealed components that were annealed at approximately 1000° C. for at least two hours in an ultra-high vacuum annealing system.

21. The electrode according to claim 18 further including a layer of material that includes zirconium deposited over said electrically conductive material.

22. The electrode according to claim 18 further including a protective layer deposited over said electrically conductive layer.

23. The electrode according to claim 22 wherein said adhesive layer is a first layer formed from a material that includes zirconium and further wherein the electrode includes a second layer of material that includes zirconium disposed between said protective layer and said conductive layer.

24. The electrode according to claim 22 wherein the electrode is included in a Surface Acoustic Wave (SAW) device and further wherein said substrate is formed from a material selected from the group of the LGX family of crystals and gallium phosphate crystals, the substrate having a SAW propagation surface upon which said adhesive and electrically conductive layers are deposited.

25. The electrode according to claim 22 wherein the electrode is included in a semiconductor device.

26. An ultra-thin electrode comprising:
a substrate;
an adhesive layer formed from a material that includes zirconium deposited upon said substrate; and
an electrically conductive layer deposited upon said adhesive layer that is formed from a material having an excellent thermal stability and a high melting temperature, said electrically conductive layer being a single composite layer of platinum-rhodium and zirconium formed by depositing a platinum-rhodium alloy simultaneously with zirconium upon said adhesive layer in an atmosphere containing oxygen.

27. The electrode according to claim 26 further including a layer of material that includes zirconium deposited over said electrically conductive material.

28. The electrode according to claim 26 further including a protective layer deposited over said electrically conductive layer.

29. The electrode according to claim 28 wherein said adhesive layer is a first layer formed from a material that includes zirconium and further wherein the electrode includes a second layer of material that includes zirconium disposed between said protective layer of SialON and said conductive layer.

30. The electrode according to claim 28 wherein the electrode is included in a Surface Acoustic Wave (SAW) device and further wherein said substrate is formed from a material selected from the group of the LGX family of crystals and gallium phosphate crystals, the substrate having a SAW propagation surface upon which said adhesive and electrically conductive layers are deposited.

31. The electrode according to claim 28 wherein the electrode is included in semiconductor device.

32. The electrode according to claim 3 wherein said adhesive layer is a first layer formed from a material that includes zirconium and further wherein the electrode includes a second layer of material that includes zirconium disposed between said protective layer and said electrically conductive layer.

33. The electrode according to claim 28 wherein said protective layer includes SiAlON.

* * * * *